(12) United States Patent
Simoneau et al.

(10) Patent No.: US 7,642,277 B2
(45) Date of Patent: *Jan. 5, 2010

(54) NON-NUCLEOSIDE REVERSE TRANSCRIPTASE INHIBITORS

(75) Inventors: Bruno Simoneau, Laval (CA); Anne-Marie Faucher, St-Placide (CA); Serge Landry, St-Jérôme (CA); Jeffrey O'Meara, Boisbriand (CA); Bounkham Thavonekham, Longueuil (CA); Christiane Yoakim, Laval (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 767 days.

This patent is subject to a terminal disclaimer.

(21) Appl. No.: 10/719,369

(22) Filed: Nov. 21, 2003

(65) Prior Publication Data

US 2005/0054639 A1 Mar. 10, 2005

Related U.S. Application Data

(60) Provisional application No. 60/430,796, filed on Dec. 4, 2002.

(51) Int. Cl.
*A61K 31/43* (2006.01)
*A61K 31/44* (2006.01)
*C07D 257/00* (2006.01)
*C07D 401/00* (2006.01)

(52) U.S. Cl. .................. 514/381; 514/349; 548/251; 546/268.4

(58) Field of Classification Search .......... 514/381, 514/349; 548/251; 546/268.4
See application file for complete search history.

(56) References Cited

U.S. PATENT DOCUMENTS 4,399,285 A 8/1983 Forster et al.
6,124,307 A 9/2000 Vig et al.
2006/0135556 A1* 6/2006 Girardet et al. ............. 514/307

FOREIGN PATENT DOCUMENTS

| CA | 2053512 A1 | 4/1992 |
| CA | 2156420 A1 | 9/1994 |
| CA | 2301800 A1 | 4/1999 |
| CA | 2375261 A1 | 12/2000 |
| CA | 2496565 A1 | 4/2004 |
| EP | 0029183 A1 | 11/1980 |
| WO | WO 99/55676 | 11/1999 |
| WO | WO 00/03998 | 1/2000 |
| WO | WO 02/32889 A1 | 4/2002 |
| WO | WO 02/070470 A2 | 9/2002 |
| WO | 2004030611 A2 | 4/2004 |

OTHER PUBLICATIONS

Irene M. Lagoja et al; 1,2,4-Triazole Derivatives Inhibiting the Human Immunodeficiency Virus Type 1 (HIV-1) in vitro; Helvetica Chimca Acta (2002) vol. 85 No. 7 pp. 1883-1892; Rega Institute for Midical Research.
International Search Report Reference No. PCT/CA 03/01870.
CAS Registry No. 310456-59-8.

* cited by examiner

*Primary Examiner*—Shengjun Wang
(74) *Attorney, Agent, or Firm*—Michael P. Morris; Mary-Ellen M. Devlin; Alan R. Stempel

(57) ABSTRACT

Disclosed herein are compounds of formula $Ar^1$—X—W—$Ar^2$ wherein $Ar^1$ and $Ar^2$ represent aryl groups characterized generally as aromatic heterocycles (e.g. imidazolyl or tetrazolyl) or carbocycles (e.g. phenyl or naphthalenyl); the aryl groups are optionally substituted or fused with other heterocycles or carbocycles; the aryl groups can bear substituents such as alkyl, halo or O-alkyl. X is a heteroatom, a valence bond or an optionally substituted divalent methylene, and W represents a spacer; typical spacers include divalent alkylene or alkylene-amido, -amido or -oxy radicals, which may optionally be substituted (e.g. hydroxyl or oxo). A typical compound is a derivative of 2-(N-napthalenyltetrazolylthio)-N-(2-nitrophenyl)acetamide. The compounds have inhibitory activity against Wild Type and single or double mutant strains of HIV.

10 Claims, No Drawings

US 7,642,277 B2

NON-NUCLEOSIDE REVERSE TRANSCRIPTASE INHIBITORS

RELATED APPLICATIONS

Benefit of U.S. Provisional Application No. 60/430,796, filed Dec. 4, 2002 is hereby claimed.

TECHNICAL FIELD OF THE INVENTION

The invention relates to compounds and pharmaceutically acceptable salts thereof, their use, either alone or in combination with other therapeutic agents, in the treatment or prophylaxis of HIV infection, and to pharmaceutical compositions comprising the compounds that are active against HIV wild type and NNRTI resistant mutants.

BACKGROUND OF THE INVENTION

The disease known as acquired immune deficiency syndrome (AIDS) is caused by the human immunodeficiency virus (HIV), particularly the strain known as HIV-1. In order for HIV to be replicated by a host cell, the information of the viral genome must be integrated into the host cell's DNA. However, HIV is a retrovirus, meaning that its genetic information is in the form of RNA. The HIV replication cycle therefore requires a step of transcription of the viral genome (RNA) into DNA, which is the reverse of the normal chain of events. An enzyme that has been aptly dubbed reverse transcriptase (RT) accomplishes the transcription of the viral RNA into DNA. The HIV virion includes copies of RT along with the viral RNA.

Reverse transcriptase has three known enzymatic functions; it acts as an RNA-dependent DNA polymerase, as a ribonuclease, and as a DNA-dependent DNA polymerase. Acting as an RNA-dependent DNA polymerase, RT transcribes a single-stranded DNA copy of the viral RNA. Acting as a ribonuclease, RT destroys the original viral RNA, and frees the DNA just produced from the original RNA. Finally, acting as a DNA-dependent DNA polymerase, RT makes a second, complementary DNA strand, using the first DNA strand as a template. The two strands form double-stranded DNA, which is integrated into the host cell's genome by another enzyme called integrase.

Compounds that inhibit the enzymatic functions of HIV-1 reverse transcriptase will inhibit replication of HIV-1 in infected cells. Such compounds are useful in the prevention or treatment of HIV-1 infection in human subjects, as demonstrated by known RT inhibitors such as 3'-azido-3'-deoxythymidine (AZT), 2',3'-dideoxyinosine (ddI), 2',3'-dideoxycytidine (ddC), d4T, 3TC, Nevirapine, Delavirdine, Efavirenz, Abacavir, and Tenofovir, the main drugs thus far approved for use in the treatment of AIDS.

As with any antiviral therapy, use of RT inhibitors in the treatment of AIDS eventually leads to a virus that is less sensitive to the given drug. Resistance (reduced sensitivity) to these drugs is the result of mutations that occur in the reverse transcriptase segment of the pol gene. Several mutant strains of HIV have been characterised, and resistance to known therapeutic agents is believed to be due to mutations in the RT gene. One of the more commonly observed mutants clinically for the non-nucleoside reverse transcriptase inhibitors, is the K103N mutant, in which a lysine (K), at codon 103, has been mutated to a asparagine (N) residue. Other mutants, which emerge with varying frequency during treatment using known antivirals, include single mutants Y181C, G190A, Y188C, and P236L, and double mutants K103N/Y181C, K103N/P225H, K103N/V108I and K103N/L100I.

As antiviral use in therapy and prevention of HIV infection continues, the emergence of new resistant strains is expected to increase. There is therefore an ongoing need for new inhibitors of RT, which have different patterns of effectiveness against the various resistant mutants.

The compounds of this invention can be characterized as being two aryl groups linked by a spacer. Relatively speaking, the structure of the linked diaryl compounds is much simpler than previously reported HIV-1 reverse transcriptase inhibitors. Accordingly, the finding of this activity for the linked diaryl compounds is surprising. In fact, the general class of linked diaryl compounds have most often been described as photographic agents. For example, EP 0436190, U.S. Pat. No. 5,124,230 and U.S. Pat. No. 6,221,573. Only a few publications have reported pharmacodynamic or therapeutic properties for this class. Such references can be summarized as follows:

U.S. Pat. No. 4,186,131 and U.S. Pat. No. 4,252,815 disclose that certain (phenyltetrazolyloxy)propyl arylamines possess antiarrhythmic and β-adrenergic blocking actions.

U.S. Pat. No. 4,399,285 relates to substituted tetrazolyloxycarboxylic acid amides which are stated to be herbicides.

Kejha et al., Cesk. Farm., 39,294(1990) reported that a series of 1-phenyl-5-thio derivatives exhibited analgesic activity.

Toth and Simon, Monatsh. Chem., 125(8-9), 977 (1994) report that certain carbamic acid esters linked with tetrazole-5 thiol exhibit pesticidal, herbicidal and antifungal activities.

U.S. Pat. No. 5,990,126 discloses that certain diarylsulfide derivatives are N-methyl-D-aspartic acid receptor antagonists.

U.S. Pat. No. 6,245,817 B1 and related WO 98/35955 disclose that α-alkoxyamide and α-thioalkoxyamide compounds are antagonists of the NPY5 receptor, and consequently the compounds are useful for treating obesity related disorders.

WO 01/16357A2 reports that N-(4-methoxyphenyl)-2-{(1-phenyl-1H-tetrazol-5-yl)thio}-acetamide is an inhibitor of sugar alcohol phosphatases with possible application as an antifungal agent.

EP 0 035 046 B1 and related U.S. Pat. Nos. 4,540,703, 4,663,323 and 4,766,120 describe tetrazole derivatives having a further unsaturated heterocylic ring; the derivatives are claimed to be antiulcer and antiinflammatory drugs.

Lagoja et al., Helv. Chim. Acta, 85, 1883 (2002) relates to a series of 1,2,4-triazole derivatives which inhibit HIV-1, HIV-2 and SIV replication.

Also, WO 02/070470 discloses a series of benzophenone bridged triaryl derivatives as HIV reverse transcriptase inhibitors, useful for treating viral infections.

In addition, a search of the CAS Chemical Registry System (2002) revealed the structures but no utility of a number of N-aryl-2-arylacetamide derivatives. For example, 2-{{1-(1-naphthalenyl)-1H-tetrazol-5-yl}thio}-N-(2-nitrophenyl)acetamide, Registry No.: 310456-59-8; N-(4-bromophenyl)-2-{{1-(3,4-dimethylphenyl)-1H-tetrazol-5-yl}thio}acetamide, Registry No.: 431890-67-4; 2-{{1-(2,4-difluorophenyl)-1H-tetrazol-5-yl}thio}-N-(2, 6-dimethylphenyl)acetamide, Registry No.: 335207-29-9; and N-(2, 4, 6-trimethylphenyl)-2-

{{1-(2, 4, 6-trimethylphenyl)-1H-tetrazol-5-yl}thio}acetamide, Registry No. 385383-12-0.

SUMMARY OF THE INVENTION

The invention provides a method for treating HIV infection comprising administering to a human infected by HIV, a therapeutically effective amount of a compound of this invention. The compounds are potent inhibitors of wild-type (WT) and double mutant strains of HIV-1 RT, particularly the double mutation K103N/Y181C.

In a first aspect the invention provides a method for treating HIV infection comprising administering to an infected human a therapeutically effective amount of a compound represented by formula 1:

$$Ar^1—X—W—Ar^2 \qquad (1)$$

wherein $Ar^1$ is
(i) 5- or 6-membered aromatic heterocycle containing 1 to 4 heteroatoms selected from N, O or S; said heterocycle optionally substituted with $(C_{1-4})$alkyl, $(C_{3-7})$cycloalkyl, $(C_{3-7})$cycloalkyl-$(C_{1-3})$alkyl-, wherein said alkyl, cycloalkyl or cycloalkylalkyl may be monosubstituted with —OH; and/or phenyl when the heterocycle contains 1 to 3 N-atoms; in either instance, the said heterocycle is optionally substituted with:
  phenyl, phenylmethyl, 5- or 6-membered aromatic heterocycle, fused phenyl-unsaturated or saturated 5- or 6-membered carbocycle, fused phenyl-{unsaturated or saturated 5- or 6-membered carbocycle}methyl, or fused phenyl-5- or 6-membered aromatic heterocycle; each of said phenyl, phenylmethyl, aromatic heterocycle, fused phenyl-carbocycle, fused phenyl-(carbocycle)methyl or fused phenyl-aromatic heterocycle in turn is substituted optionally with 1 to 3 substituents selected independently from:
    $(C_{1-6})$alkyl, $(C_{3-7})$cycloalkyl, $(C_{3-7})$cycloalkyl-$(C_{1-3})$alkyl, $(C_{2-6})$alkenyl, O—$(C_{1-4})$alkyl, S—$(C_{1-4})$alkyl, halo, $CF_3$, $OCF_3$, OH, $NO_2$, CN, phenyl optionally substituted with $C_{1-6}$-alkyl or nitro, phenylmethyl optionally substituted with $C_{1-6}$alkyl or nitro, $SO_2NH_2$, $SO_2$—$(C_{1-4})$alkyl, $C(O)NH_2$, $C(O)OR^1$, $NR^2R^3$, morpholino or 1-pyrrolyl,
    wherein $R^1$ is H or $(C_{1-4})$alkyl, and wherein $R^2$ and $R^3$ each independently is H or $(C_{1-4})$alkyl; wherein said substituents are sterically compatible; or
(ii) unsaturated or saturated 5- or 6-membered carbocycle substituted with phenyl or naphthyl, said unsaturated or saturated carbocycle, or the phenyl or naphthyl optionally substituted with the same 1 to 3 substituents as defined for the substituents in section (i); or
(iii) benzimidazole optionally N-substituted with phenyl or a fused phenyl-carbocycle as defined above;
X is a heteroatom selected from O, S, SO, $SO_2$ or $NR^4$ wherein $R^4$ is H or $(C_{1-4})$alkyl; or X is a valence bond or $CR^{4A}R^{4B}$ wherein $R^{4A}$ and $R^{4B}$ each independently is H or $(C_{1-4})$alkyl; and when X is a heteroatom, including $NR^4$:
W is a divalent radical selected from:
(a) $(CR^5R^{5A})_{1-2}$—$C(Z^A)NR^6$ wherein $R^5$ and $R^{5A}$ each independently is H or $(C_{1-4})$alkyl, $R^6$ is H or $(C_{1-4})$alkyl, and $Z^A$ is oxo or thioxo;
(b) D-C($Z^B$) wherein D is $(C_{1-4})$alkylene, $(C_{1-4})$alkylene-O or $(C_{1-4})$alkylene-$NR^7$ wherein $R^7$ is H or $(C_{1-4})$alkyl, and $Z^B$ is oxo or thioxo;
(c) $CH_2C(Z^C)NR^{7A}$—$(C_{1-4})$alkylene wherein $Z^C$ is oxo or thioxo and $R^{7A}$ is H or $(C_{1-4})$alkyl;
(d) $(C_{1-4})$alkylene-$NR^{7B}C(Z^D)NR^{7C}$ wherein $R^{7B}$ and $R^{7C}$ each independently is H or $(C_{1-4})$alkyl, and $Z^D$ is oxo or thioxo;
(e) $(C_{1-4})$alkylene optionally substituted with OH, or optionally disubstituted with OH when the $(C_{1-4})$alkylene contains 2 to 4 carbon atoms; $(C_{2-4})$alkenyl optionally substituted with halo; or
cis- or trans-

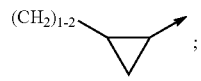

or
(f) {$(C_{1-4})$alkylene}-O optionally substituted on the alkylene portion with OH;
(g) {$(C_{1-4})$alkylene}-$NR^8$ optionally substituted on the alkylene portion with OH, and $R^8$ is H or $(C_{1-4})$alkyl;
(h) $(C_{1-4})$alkylene-$C(Z^E)(C_{1-4})$alkylene wherein $Z^E$ is oxo or thioxo; or
(i)

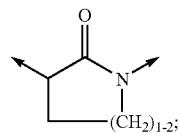

or
(j) $(CR^5R^{5A})_{1-2}$—$NR^6$—$(CR^5R^{5A})_{1-2}$ wherein $R^5$ and $R^{5A}$ each independently is H or $(C_{1-4})$alkyl, $R^6$ is H or $(C_{1-4})$alkyl; or when X is a valence bond:
W is a {$(C_{2-4})$alkenyl}$C(O)NR^{8A}$,
cis- or trans-

or
cis- or trans-

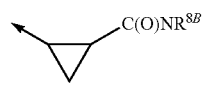

wherein $R^{8A}$ and $R^{8B}$ each is H or $(C_{1-4})$alkyl; or
when X is $CR^{4A}R^{4B}$ as defined above:
W is selected from {$(C_{1-4})$alkylene}$C(O)NR^{8C}$, S—{$(C_{1-4})$alkylene}$C(O)NR^{8D}$, O-{$(C_{1-4})$-alkylene}$C(O)NR^{8E}$, or $NR^{8F}$-{$(C_{1-4})$alkylene}-$NR^{8G}$, wherein $R^{8C}$, $R^{8D}$, $R^{8E}$, $R^{8F}$ and $R^{8G}$ each independently is H or $(C_{1-4})$alkyl; and Ar² is
(i) a phenyl or pyridinyl selected from the formulas

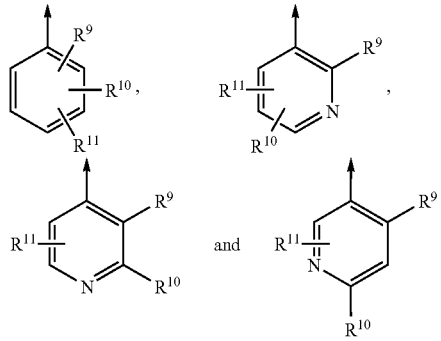

wherein R⁹, R¹⁰ and R¹¹ each independently represents:
  H, $(C_{1-6})$alkyl, $(C_{3-7})$cycloalkyl, $(C_{3-7})$cycloalkyl-$(C_{1-3})$alkyl, $(C_{2-4})$alkenyl, O—$(C_{1-6})$alkyl, S—$(C_{1-6})$alkyl, halo, $CF_3$, $OCF_3$, OH, $NO_2$, CN, —$NR^{N1}R^{N2}$, —C(O)R²¹, —$(C_{1-3})$alkyl-C(O)R²¹, —C(O)OR²², —$(C_{1-3})$alkyl-C(O)OR²², —$SO_2$—$(C_{1-3})$alkyl-C(O)OR²², wherein R²¹ is $(C_{1-4})$alkyl and R²² is H or $(C_{1-4})$alkyl; C(O)NH₂, —$(C_{1-3})$alkyl-C(O)NH₂, S(O)—$(C_{1-4})$alkyl, $SO_2$—$(C_{1-4})$alkyl, $SO_2NH_2$, phenyl, phenylmethyl, phenyl-$SO_2$—, 2-, 3- or 4-pyridinyl, 1-pyrrolyl, whereby said phenyl, pyridinyl and pyrrolyl may have one or more substituents selected from the group consisting of halo, $NO_2$, $C_{1-3}$-alkyl and $CF_3$;
  wherein the substituents R⁹, R¹⁰ and R¹¹ are sterically compatible;
  wherein $R^{N1}$, $R^{N2}$ each independently represent H or $(C_{1-6})$alkyl, whereby $R^{N1}$ and $R^{N2}$ may be covalently bonded to each other to form together with the N-atom to which they are attached to a 4 to 7-membered heterocycle whereby the —CH₂-group at the position 4 of a 6 or 7-membered heterocycle may be replaced by —O—, —S— or —$NR^{N3}$— wherein $R^{N3}$ represents H, —C(O)OR²², $(C_{1-6})$alkyl, $(C_{3-7})$cycloalkyl or $(C_{3-7})$cycloalkyl-$(C_{1-3})$alkyl, wherein R²² is H or $(C_{1-4})$alkyl; or
(ii) Ar² is a fused phenyl-(saturated or unsaturated 5- or 6-membered carbocyclic ring optionally substituted with 1 to 3 substituents selected independently from $(C_{1-4})$alkyl, O—$(C_{1-4})$alkyl, S—$(C_{1-4})$alkyl, $NO_2$ or halo; or
(iii) Ar² is a 5- or 6-membered aromatic heterocycle containing 1 to 4 heteroatoms selected from N, O or S, or a fused phenyl-5- or 6-membered heterocycle, said aromatic heterocycle or fused phenyl-heterocycle is optionally substituted with 1 to 3 substituents selected independently from $(C_{1-4})$alkyl, O—$(C_{1-4})$alkyl, S—$(C_{1-4})$alkyl, $NO_2$ or halo; or
(iv) Ar² is phthalimido and W is $(C_{1-4})$alkylene;

or a pharmaceutically acceptable salt, ester or prodrug thereof.

Furthermore, a second aspect of this invention provides compounds of formula 1:

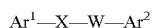   1 wherein Ar¹ is

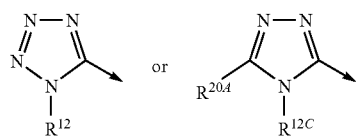

wherein R¹² is selected from the group consisting of

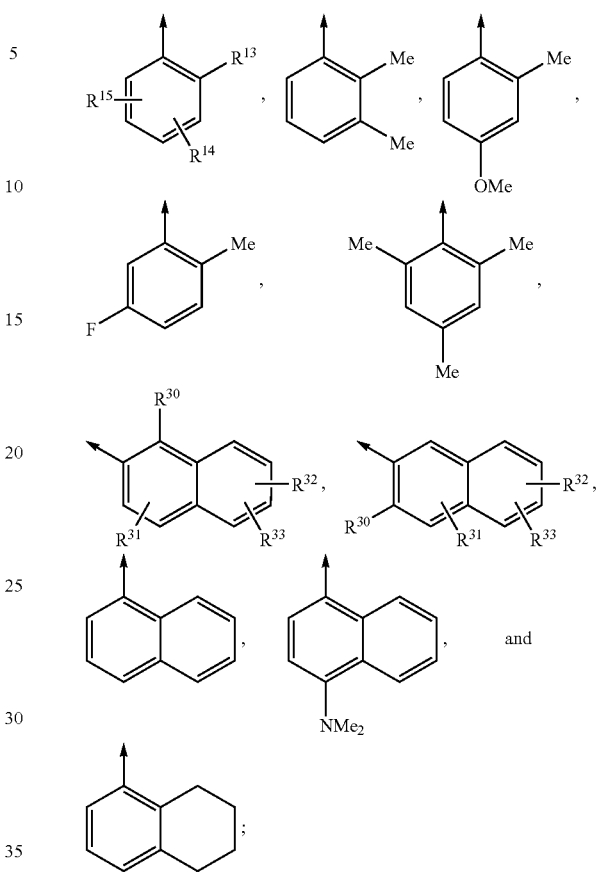

R¹³ represents Cl, Br, $COO(C_{1-4})$alkyl and
if R⁹ is $NO_2$, Cl or Br, then R¹³ may also represent F or $CH_3$;
R¹⁴, R¹⁵,
R³¹, R³²,
R³³ are each independently selected from the group consisting of H, $(C_{1-6})$alkyl, $(C_{3-7})$cycloalkyl, $(C_{3-7})$cycloalkyl-$(C_{1-3})$alkyl, $(C_{2-6})$alkenyl, O—$(C_{1-4})$alkyl, S—$(C_{1-4})$alkyl, halo, $CF_3$, $OCF_3$, OH, $NO_2$, CN, $SO_2NH_2$, $SO_2$—$(C_{1-4})$alkyl, $C(O)OR^1$ wherein $R^1$ is H or $(C_{1-4})$alkyl, or $NR^2R^3$ wherein $R^2$ and $R^3$ each independently is H or $(C_{1-4})$alkyl;
R³⁰ represents H, Cl, Br, $COO(C_{1-4})$alkyl;
$R^{12C}$ is a phenyl of formula

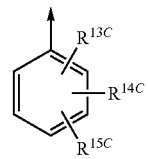

wherein $R^{13C}$, $R^{14C}$ and $R^{15C}$ each independently represents H, $(C_{1-6})$alkyl, $(C_{3-7})$cycloalkyl, $(C_{3-7})$cycloalkyl-$(C_{1-3})$alkyl, $(C_{2-6})$alkenyl, O—$(C_{1-4})$alkyl, S—$(C_{1-4})$alkyl, halo, $CF_3$, $OCF_3$, OH, $NO_2$, CN, $SO_2NH_2$, $SO_2$—$(C_{1-4})$alkyl, $C(O)OR^1$ wherein $R^1$ is H or $(C_{1-4})$alkyl, or $NR^2R^3$ wherein $R^2$ and $R^3$ each independently is H or $(C_{1-4})$alkyl; provided that at least one of $R^{13C}$, $R^{14C}$ and $R^{15C}$ is other than hydrogen; or $R^{12C}$ is

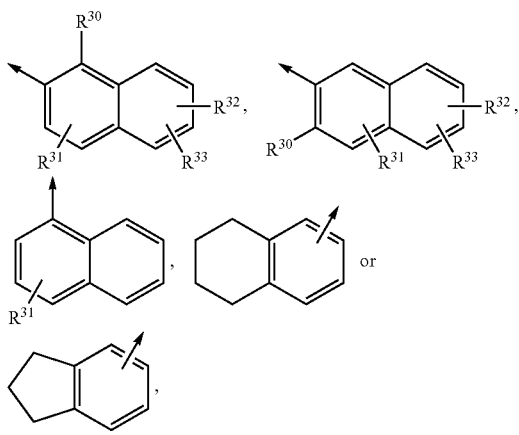

wherein R³⁰, R³¹, R³², R³³ are as defined hereinbefore; and R²⁰ᴬ is H, (C₁₋₄)alkyl, (C₃₋₇)cycloalkyl or (C₃₋₇)cycloalkyl-(C₁₋₃)alkyl-, wherein said alkyl, cycloalkyl or cycloalkylalkyl may be monosubstituted with —OH; and X is S or O;

W is CH₂C(O)NR⁶ wherein R⁶ is H or (C₁₋₄)alkyl; and Ar² is selected from the group consisting of

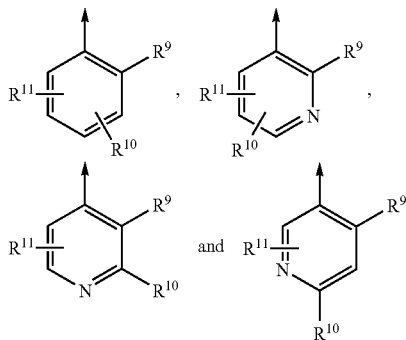

wherein R⁹ is halo or NO₂; and if R¹³ is Cl or Br, then R⁹ may also represent (C₁₋₃)alky;

R¹⁰, R¹¹ are independently of each other selected from the group consisting of H, (C₁₋₆)alkyl, (C₃₋₇)Cycloalkyl, (C₃₋₇)Cycloalkyl-(C₁₋₃)alkyl, (C₂₋₆)alkenyl, O(C₁₋₆)alkyl, S(C₁₋₆)alkyl, halo, CF₃, OCF₃, OH, NO₂, CN, —NR^{N1}R^{N2}, —C(O)R²¹, —(C₁₋₃)alkyl-C(O)R²¹, —C(O)OR²², —(C₁₋₃)alkyl-C(O)OR²², —SO₂—(C₁₋₃)alkyl-C(O)OR²², wherein R²¹ is (C₁₋₄)alkyl and R²² is H or (C₁₋₄)alkyl; —(C₁₋₃)alkyl-C(O)NH₂,C(O)NH₂, S(O)—(C₁₋₆)alkyl, —SO₂—(C₁₋₆)alkyl, —SO₂-phenyl, —SO₂—NH₂, phenyl, phenylmethyl, 2-, 3- or 4-pyridinyl, 1-pyrrolyl, whereby said phenyl, pyridinyl and pyrrolyl may have one or more substituents selected from the group consisting of halo, NO₂, C₁₋₃-alkyl and CF₃;

or a pharmaceutically acceptable salt, ester or prodrug thereof.

According to another aspect of the invention, there is provided the use of a compound of formula 1 as defined hereinbefore and hereinafter, or a pharmaceutically acceptable salt, ester or prodrug thereof, for the manufacture of a medicament for the treatment or prevention of an HIV infection.

According to yet another aspect of the invention, there is provided the use of a compound of formula 1 as defined hereinbefore and hereinafter, or a pharmaceutically acceptable salt, ester or prodrug thereof, in combination with one or more other antiretroviral drugs.

According to a further aspect of the invention, there is provided a pharmaceutical composition, comprising a compound of formula 1 as defined hereinbefore and hereinafter, or a pharmaceutically acceptable salt, ester or prodrug thereof, and optionally one or more pharmaceutically acceptable carriers.

According to another aspect of the invention, there is provided a pharmaceutical composition for the treatment or prevention of HIV infection, comprising a compound of formula 1 as defined hereinbefore and hereinafter, or a pharmaceutically acceptable salt, ester or prodrug thereof, and optionally one or more pharmaceutically acceptable carriers.

According to a sixth aspect of the invention, there is provided a process for preparing a compound of formula 1 wherein Ar¹ and Ar² are as defined hereinbefore and hereinafter, X is S or O and W is (CR⁵R⁵ᴬ)₁₋₂C(O)NR⁶, wherein R⁵, R⁵ᴬ and R⁶ each independently is H or (C₁₋₄)alkyl, comprising:

a) reacting a thiol or alcohol of formula Ar¹—X—H with an ω-halo alkanoic alkyl ester of formula Y—(CR⁵R⁵ᴬ)₁₋₂C(O)ORᴬ wherein Y is halo and Rᴬ is (C₁₋₄)alkyl, in the presence of a base, to obtain the corresponding ester of formula Ar¹—X—(CR⁵R⁵)₁₋₂C(O)ORᴬ, followed by hydrolysis of the ester to the corresponding acid wherein Rᴬ=H, and coupling the latter acid with an aromatic amine of general formula HNR⁶—Ar² in the presence of a coupling agent to obtain the corresponding compound of formula 1 wherein Ar¹, Ar², X and W are as defined herein; or b) reacting a thiol or alcohol of formula Ar¹—X—H wherein Ar¹ and X are as defined herein with an anilide of formula Y—(CR⁵R⁵ᴬ)₁₋₂C(O)NR⁶—Ar² wherein Y, R⁵, R⁵ᴬ, R⁶ and Ar¹ are as defined herein, in the presence of a base to obtain the corresponding compound of formula 1.

DETAILED DESCRIPTION OF THE INVENTION

Definitions

The following definitions apply unless otherwise noted:

As used herein, the term "(C₁₋₄)alkyl", either alone or in combination with another radical, is intended to mean acyclic straight or branched chain alkyl radicals containing from one to four carbon atoms respectively. Examples of such radicals include methyl (Me), ethyl (Et), propyl (Pr), 1-methylethyl (iPr), butyl (Bu), 2-methylpropyl (iBu), and 1,1-dimethylethyl (tBu), wherein the abbreviations commonly used herein are given in brackets.

As used herein, the term "O—(C₁₋₄)alkyl", either alone or in combination with another radical, refers to alkoxy radicals containing for one to four carbon atoms and includes methoxy (OMe), ethoxy (OEt), propoxy (OPr), 1-methylethoxy (OiPr), butoxy (OBu) and 1,1-dimethylethoxy (OtBu), wherein the abbreviations commonly used herein are given in brackets.

As used herein, the term "S—(C₁₋₄)alkyl", either alone or in combination with another radical, refers to alkylthio, radicals containing one to four carbon atoms and includes methylthio, ethylthio, propylthio, (1-methylethyl)thio, butylthio and (1,1-dimethylethyl)thio.

As used herein, the term "halo" means a halo radical selected from bromo, chloro, fluoro or iodo.

As used herein, the term "$(C_{1-4})$alkylene," either alone or in combination with another radical, means a divalent alkyl radical derived by removal of two hydrogens atoms from an aliphatic hydrocarbon containing one to four carbon atoms and includes —$CH_2$—, —$CH_2CH_2$—, —$CH_2CH_2CH_2$—, —$CH_2CH(Me)$—, —$CH_2CH_2CH_2CH_2$— and —$CH_2CH(Me)CH_2$—.

As used herein, the term "$(C_{2-4})$alkenyl", either alone or used with antother radical, means a divalent alkene radical derived by removal of two hydrogen atoms from an olefinic hydrocarbon containing two to four carbon atoms and includes —CH=CH—, —$CH_2$CH=CH—, —$CH_2$CH=CH$CH_2$— and —CH(Me)CH=CH—. The cis and trans isomers, and mixtures thereof, of the $(C_{2-4})$alkenyl radical can be encompassed by the term.

As used herein, the term "unsaturated or saturated 5- or 6-membered carbocycle", either alone or in combination with another radical, means a unsaturated or saturated monocyclic hydrocarbon containing 5 to 6 carbon atoms and includes, for example, phenyl, 1-cyclohexen, 1,3-cyclohexadienyl, cyclohexanyl, 1-cyclopentenyl and cyclopentanyl. In the following Ph is used as an abbreviation for phenyl.

As used herein, the term "fused phenyl-(saturated or unsaturated 5- or 6-membered carbocycle)" or "fused phenyl-carbocycle," either alone or in combination with another radical, means a phenyl that is fused with a saturated or unsaturated 5- or 6-membered carbocyclic ring. Examples include naphthalenyl, 1, 2, 3, 4-tetrahydronaphthalenyl, 2, 3-dihydro-1H-indenyl and indenyl.

As used herein, the term "aromatic heterocycle", either alone or in combination with another radical, means a monovalent radical derived by removal of a hydrogen from a 5- or 6-membered aromatic heterocycle containing, 1 to 4 heteroatoms selected from N, O and S. Examples of suitable aromatic heterocycles include tetrazolyl, pyridinyl, imidazolyl, 1,2,4-triazolyl, isoxazolyl and thiazolyl.

As used herein, the term "heterocycle", either alone or in combination with another radical, is intended to mean a monovalent radical derived by removal of a hydrogen from a 5- or 6-membered saturated or unsaturated (including aromatic) heterocycle containing 1 to 4 heteroatoms selected from N, O and S. Examples of suitable heterocycles include 1,3-dioxolanyl, pyrrolidinyl, pyrazolyl and thiazolyl.

As used herein, the term "fused phenyl-5- or 6-membered aromatic heterocyle", either alone or in combination with another radical, is intended to mean a phenyl that is fused with a 5- or 6-membered aromatic heterocycle having 1 to 2 nitrogen atoms. Examples include 1H-benzimidazolyl, quinolinyl and isoquinolinyl.

As used herein, the term "inhibitor of HIV replication" refers to an agent capable of substantially reducing or essentially eliminating the ability of HIV-1 reverse transcriptase to replicate a DNA copy from an RNA template.

As used herein, the term "single or double mutant strains" means that either one or two amino acid residues that are present in WT HIV-1 strain have been replaced by residues not found in the WT strain. For example, the single mutant Y181C is prepared by site-directed mutagenesis in which the tyrosine at residue 181 has been replaced by a cysteine residue. Similarly, for the double mutant K103N/Y181C, an asparagine residue has replaced the lysine at residue 103 and a cysteine residue has replaced the tyrosine at residue 181.

As used herein, the term "pharmaceutically acceptable salt" means a salt of a compound which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. Where applicable and compatible with the chemical properties of the compound of formula 1, the term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1-19, which is hereby incorporated by reference in its entirety.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic non-toxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N' dibenzylethylenediamine, polyamine resins, and the like. Particularly preferred organic nontoxic bases are isopropylamine, diethylamine, ethanolamine, trimethylamine, dicyclohexylamine, choline, and caffeine.

When a valence bond on a phenyl ring or heterocyclic ring is illustrated as follows:

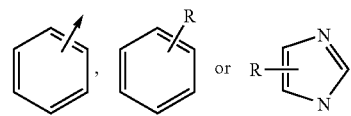

then the indication is that the valence bond can replace any hydrogen atom on the ring.

As used herein, the term "prodrug" refers to pharmacologically acceptable derivatives, such that the resulting biotransformation product of the derivative is the active drug, as defined in compounds of formula 1: Examples of such derivatives include, but are not limited to, esters and amides (see Goodman and Gilman in The Pharmacological Basis of Therapeutics, 9th ed., McGraw-Hill, Int. Ed. 1995, "Biotransformation of Drugs, p 11-16, incorporated herein by reference).

DETAILED DESCRIPTION OF PREFERRED EMBODIMENTS

According to a first embodiment of the first aspect of the present invention there is provided a method for treating HIV infection comprising administering to an infected human a therapeutically effective amount of a compound represented by formula 1:

$$Ar^1\text{—}X\text{—}W\text{—}Ar^2 \qquad 1$$

wherein $Ar^1$ is
(i) 5- or 6-membered aromatic heterocycle containing 1 to 4 heteroatoms selected from N, O or S; said heterocycle optionally substituted with $(C_{1-4})$alkyl or phenyl when the heterocycle contains 1 to 3 N-atoms; in either instance, the said heterocycle is optionally substituted with:
   phenyl, phenylmethyl, 5- or 6-membered aromatic heterocycle, fused phenyl-unsaturated or saturated 5- or 6-membered carbocycle, fused phenyl-{unsaturated or saturated 5- or 6-membered carbocycle}methyl, or fused phenyl-5- or 6-membered aromatic heterocycle; each of said phenyl, carbocycle or heterocycle, in turn is substituted optionally with 1 to 3 substituents selected independently from:
   $(C_{1-4})$alkyl, O—$(C_{1-4})$alkyl, S—$(C_{1-4})$alkyl, halo, $CF_3$, OH, $NO_2$, CN, phenyl optionally substituted with $(C_{1-6})$alkyl, $SO_2NH_2$, $SO_2$—$(C_{1-4})$alkyl, $C(O)OR^1$ wherein $R^1$ is H or $(C_{1-4})$alkyl, or $NR^2R^3$ wherein $R^2$ and $R^3$ each independently is H or $(C_{1-4})$alkyl; wherein said substituents are sterically compatible; or
(ii) unsaturated or saturated 5- or 6-membered carbocycle substituted with phenyl or naphthyl, said unsaturated or saturated carbocycle, or the phenyl or naphthyl optionally substituted with the same 1 to 3 substituents as defined for the substituents in section (i); or
(iii) benzimidazole optionally N-substituted with phenyl or a fused phenyl-carbocycle as defined above;

X is a heteroatom selected from O, S or $NR^4$ wherein $R^4$ is H or $(C_{1-4})$alkyl; or X is a valence bond or $CR^{4A}R^{4B}$ wherein $R^{4A}$ and $R^{4B}$ each independently is H or $(C_{1-4})$alkyl; and when X is a heteroatom:
W is a divalent radical selected from:
(a) $(CR^5R^{5A})_{1-2}$—$C(Z^A)NR^6$ wherein $R^5$ and $R^{5A}$ each independently is H or $(C_{1-4})$alkyl, $R^6$ is H or $(C_{1-4})$alkyl, and $Z^A$ is oxo or thioxo;
(b) D-$C(Z^B)$ wherein D is $(C_{1-4})$alkylene, $(C_{1-4})$alkylene-O or $(C_{1-4})$alkylene-$NR^7$ wherein $R^7$ is H or $(C_{1-4})$alkyl, and $Z^B$ is oxo or thioxo;
(c) $CH_2C(Z^C)NR^{7A}$—$(C_{1-4})$alkylene wherein $Z^C$ is oxo or thioxo and $R^{7A}$ is H or $(C_{1-4})$alkyl;
(d) $(C_{1-4})$alkylene-$NR^{7B}C(Z^D)NR^{7C}$ wherein $R^{7B}$ and $R^{7C}$ each independently is H or $(C_{1-4})$alkyl, and $Z^D$ is oxo or thioxo;
(e) $(C_{1-4})$alkylene optionally substituted with OH, or optionally disubstituted with OH when the $(C_{1-4})$alkylene contains 2 to 4 carbon atoms; $(C_{2-4})$alkenyl optionally substituted with halo; or
cis- or trans-

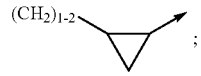

or
(f) {$(C_{1-4})$alkylene}-O optionally substituted on the alkylene portion with OH;
(g) {$(C_{1-4})$alkylene}-$NR^8$ optionally substituted on the alkylene portion with OH, and $R^8$ is H or $(C_{1-4})$alkyl;
(h) $(C_{1-4})$alkylene-$C(Z^E)(C_{1-4})$alkylene wherein $Z^E$ is oxo or thioxo; or
(i)

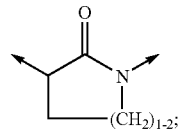

or
when X is a valence bond:
W is a {$(C_{2-4})$alkenyl}$C(O)NR^{8A}$,
cis- or trans-

wherein $R^{8A}$ and $R^{8B}$ each is H or $(C_{1-4})$alkyl; or
when X is $CR^{4A}R^{4B}$ as defined above:
W is selected from {$(C_{1-4})$alkylene}$C(O)NR^{8C}$, S—{$(C_{1-4})$alkylene}$C(O)NR^{8D}$, O—{$(C_{1-4})$-alkylene}$C(O)NR^{8E}$, or $NR^{8F}$—{$(C_{1-4})$alkylene}—$NR^{8G}$ wherein $R^{8C}$, $R^{8D}$, $R^{8E}$, $R^{8F}$ and $R^{8G}$ each independently is H or $(C_{1-4})$alkyl; and $Ar^2$ is
(i) a phenyl of formula

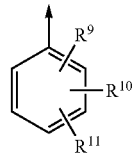

wherein $R^9$, $R^{10}$ and $R^{11}$ each independently represents:
H, $(C_{1-4})$alkyl, O—$(C_{1-4})$alkyl, S—$(C_{1-4})$alkyl, halo, $CF_3$, OH, $NO_2$, phenyl, phenylmethyl, (2-nitrophenyl)methyl, 2-methylphenyl, —C(O)—$(C_{1-4}\text{-})$alkyl, $C(O)NH_2$, S(O)—$(C_{1-4})$alkyl, $SO_2NH_2$, 2-, 3- or 4-pyridinyl, morpholino or 1-pyrrolyl, or —$C(O)OR^{22}$, wherein $R^{22}$ is H or $(C_{1-4})$alkyl; wherein the substituents $R^9$, $R^{10}$ and $R^{11}$ are sterically compatible; or
(ii) $Ar^2$ is a fused phenyl-saturated or unsaturated 5- or 6-membered carbocyclic ring optionally substituted with 1 to 3 substituents selected independently from $(C_{1-4})$alkyl, $O-(C_{1-4})$alkyl, $S-(C_{1-4})$alkyl, $NO_2$ or halo; or
(iii) $Ar^2$ is a 5- or 6-membered aromatic heterocycle containing 1 to 4 heteroatoms selected from N, O or S, or a fused phenyl-5- or 6-membered heterocycle, said aromatic heterocycle or fused phenyl-heterocycle is optionally substituted with 1 to 3 substituents selected independently from $(C_{1-4})$alkyl, $O-(C_{1-4})$alkyl, $S-(C_{1-4})$alkyl, $NO_2$ or halo; or
(iv) $Ar^2$ is phthalimido and W is $(C_{1-4})$alkylene;

or a pharmaceutically acceptable salt, ester or prodrug thereof.

According to said first embodiment the method of this invention preferably relates to a compound represented by formula 1a:

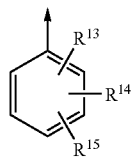

1a wherein X, W and $Ar^2$ are as defined above and $R^{12}$ is a phenyl of formula

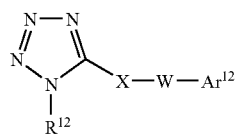

wherein $R^{13}$, $R^{14}$ and $R^{15}$ each independently represents H, $(C_{1-4})$alkyl, $O-(C_{1-4})$alkyl, $S-(C_{1-4})$alkyl, halo, $CF_3$, OH, $NO_2$, CN, Ph, 2-methylphenyl, $SO_2NH_2$, $SO_2-(C_{1-4})$alkyl, $C(O)NH_2$, morpholino, 1-pyrrolyl, $(2-NO_2Ph)CH_2$, $PhCH_2$, $C(O)OR^{16}$ wherein $R^{16}$ is H or $(C_{1-4})$alkyl; or $R^{12}$ is

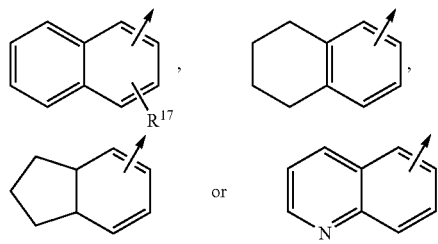

wherein $R^{17}$ is H, $(C_{1-4})$alkyl, $O-(C_{1-4})$alkyl, halo, $CF_3$ or $NR^{18}R^{19}$ wherein $R^{18}$ and $R^{19}$ each independently is H or $(C_{1-4})$alkyl.

Most preferably $R^{13}$, $R^{14}$ and $R^{15}$ each independently represents H, Me, Et, Pr, iPr, tBu, OMe, OEt, OiPr, SMe, SEt, Br, Cl, F, $CF_3$, $OCF_3$, $NO_2$, C(O)OH, C(O)OMe or C(O)OEt, provided that at least one of $R^{13}$, $R^{14}$ and $R^{15}$ is other than hydrogen.

Furthermore, most preferably $R^{17}$ is selected from H, Me, OMe, Cl, F, $CF_3$, $NH_2$, NHMe or $NMe_2$.

Regarding the method of said first embodiment, those compounds of formula 1a are more preferred wherein $R^{12}$ is selected from:

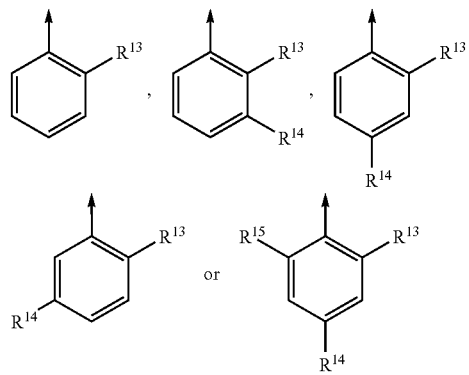

wherein $R^{13}$, $R^{14}$ and $R^{15}$ each independently is Me, Et, OMe, O-iPr, SMe, Br, Cl, F, $CF_3$ or C(O)OMe; or wherein $R^{12}$ is selected from:

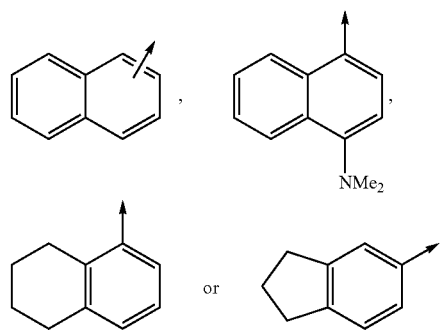

Very most preferably $R^{12}$ is selected from:

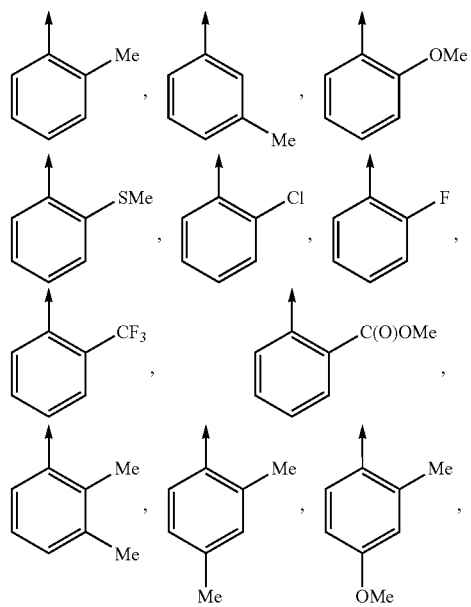

-continued

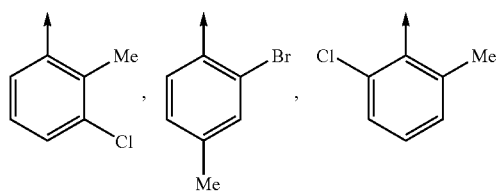

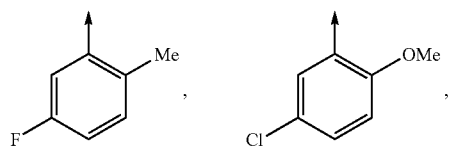

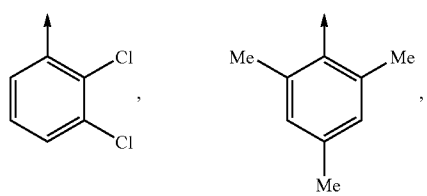

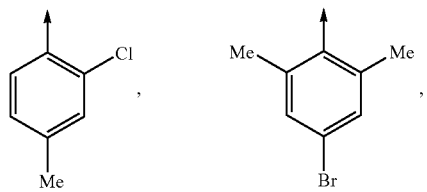

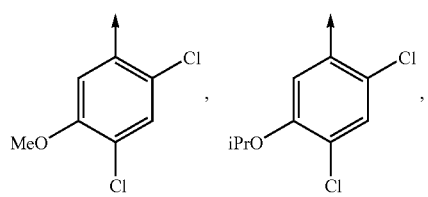

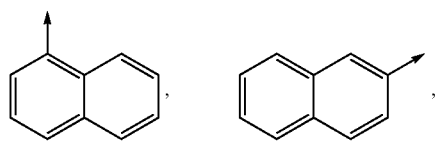

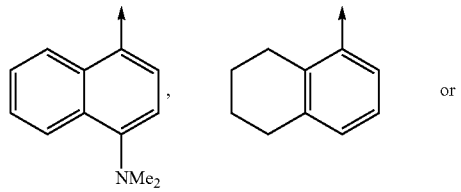

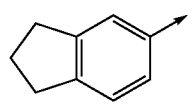

According to the first embodiment of the first aspect of this invention, alternatively the compound to be administered is preferably a compound represented by formula 1 b:

Ar³—X—W—Ar²   1b wherein X, W and Ar² are as defined hereinbefore and Ar³ is selected from the group consisting of:

wherein $R^{12A}$, $R^{12B}$, $R^{12C}$ and $R^{12D}$ each is a phenyl of formula

wherein $R^{13}$, $R^{14}$ and $R^{15}$ each independently represents H, $(C_{1-4})$alkyl, O—$(C_{1-4})$alkyl, S—$(C_{1-4})$alkyl, halo, $CF_3$, OH, $NO_2$, CN, Ph, 2-methylphenyl, $SO_2NH_2$, $SO_2$—$(C_{1-4})$alkyl, $C(O)NH_2$, morpholino, 1-pyrrolyl, (2-$NO_2$-Ph)$CH_2$, Ph$CH_2$, $C(O)OR^{16}$ wherein $R^{16}$ is H or $(C_{1-4})$alkyl; or $R^{12A}$, $R^{12B}$, $R^{12C}$ and $R^{12D}$ each is

wherein $R^{17}$ is H, $(C_{1-4})$alkyl, O—$(C_{1-4})$alkyl, halo, $CF_3$ or $NR^{18}R^{19}$ wherein $R^{18}$ and $R^{19}$ each independently is H or $(C_{1-4})$alkyl;

and $R^{20}$ and $R^{20A}$ each is H or $(C_{1-4})$alkyl.

Preferably Ar³ is represented by the formula:

wherein $R^{12C}$ is as hereinbefore and $R^{20A}$ is H, Me, Et, Pr or iPr.

Most preferably $R^{12C}$ is a phenyl of the formula

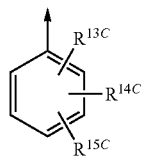

wherein $R^{13C}$, $R^{14C}$ and $R^{15C}$ each independently is H, Me, Et, Pr, iPr, OMe, OEt, SMe, SEt, Br, Cl, F, $CF_3$, $NO_2$, C(O)OH, C(O)OMe or C(O)OEt, provided that at least one of $R^{13C}$, $R^{14C}$, and $R^{15C}$ is other that hydrogen, and $R^{20A}$ is H, Me or Et; or $R^{12C}$ is

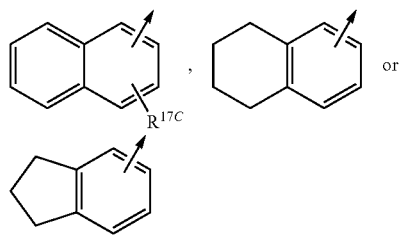

wherein $R^{17C}$ is selected from H, Me, OMe, Cl, F, $CF_3$, $NH_2$, NHMe or $NMe_2$; and $R^{20A}$ is H, Me or Et.

A method of treatment according to the present invention is preferred wherein the compound is a compound of formula 1 wherein X is O or S, most preferably S.

Preferably, the method of treatment relates to compounds of formula 1a wherein X is O or S and W is $CR^5R^{5A}$—C(O)NH wherein $R^5$ and $R^{5A}$ each is independently H or Me. More preferably, X is S and W is $CH(R^5)C(O)NH$ wherein $R^5$ is H or Me.

Preferably, the method of treatment relates to compounds of formula 1a wherein X is O or S and W is $D-C(Z^B)$ wherein D is $CH_2CH_2O$, $CH_2CH_2NH$ or $CH_2CH_2NMe$, and $Z^B$ is O. More preferably, X is S and W is $CH_2CH_2OC(O)$.

Preferably, the method of treatment relates to compounds of formula 1a wherein X is O or S and W is $CH_2CH_2CH_2$, $CH_2CH_2CH(OH)$, $CH_2CH(OH)CH_2$, trans —$CH_2CH$=CH, trans —$CH_2CF$=CH or

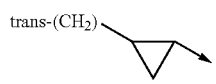

More preferably, X is S and W is $CH_2CH_2CH(OH)$, $CH_2CH(OH)CH_2$ or

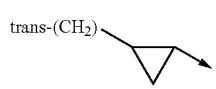

Preferably, the method of treatment relates to compounds of formula 1a wherein X is O or S and W is $CH_2CH_2O$, $CH_2CH_2CH_2O$, $CH_2CH(OH)CH_2O$, $CH_2CH_2NH$, CH(OH)$CH_2NH$, $CH_2CH_2NMe$ or $CH_2CH(OH)CH_2NH$. More preferably, X is S and W is $CH_2CH(OH)CH_2O$, $CH(OH)CH_2NH$ or $CH_2CH(OH)CH_2NH$.

Preferably, the method of treatment relates to compounds of formula 1a wherein X is a valence bond and W is CH=CHC(O)NH or

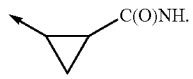

Preferably, the method of treatment relates to compounds of formula 1a, wherein X is $CH_2$ and W is $SCH_2C(O)NH$, $OCH_2C(O)NH$, $NHCH_2C(O)NH$ or $NMeCH_2C(O)NH$. More preferably X is $CH_2$ and W is $SCH_2C(O)NH$.

Most preferably, the method of treatment relates to compounds of formula 1a wherein X is S and W is $CH_2C(O)NH$, $CH(Me)C(O)NH$, $CH_2CH_2CH(OH)$, $CH_2CH(OH)CH_2$, $CH_2CH(OH)CH_2NH$ or

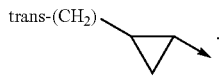

Preferably, the method of treatment relates to of compounds of formula 1a wherein $Ar^2$ is phenyl of formula:

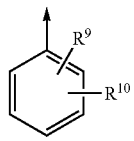

wherein $R^9$ and $R^{10}$ each independently represents H, Me, Et, iPr, OMe, OEt, SMe, SEt, Br, Cl, F, I, $CF_3$, OH, $NO_2$, CN, Ph, C(O)OH, C(O)OMe, C(O)OEt, C(O)Me, C(O)Et, C(O)$NH_2$, $SO_2Me$, $SO_2NH_2$, morpholino, 1-pyrrolyl, (2-$NO_2$Ph)$CH_2$ or $PhCH_2$. More preferably, $R^9$ is halo or $NO_2$, and $R^{10}$ is OMe, halo, OH, $NO_2$, Ph, C(O)OH or C(O)OMe.

More preferably, $Ar^2$ is selected from

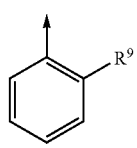

wherein $R^9$ is Me, Cl, F, Br, I or $NO_2$.

Even more preferably, $Ar^2$ is is selected from:

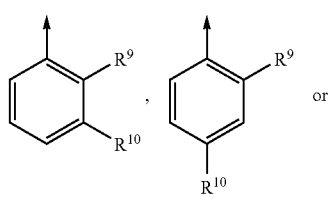

-continued

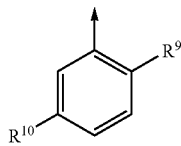

wherein $R^9$ is Me, Br, Cl, F, I or $NO_2$, and $R^{10}$ is Me, OMe, Cl, F, OH, Ph, C(O)OH, C(O)OMe or CN.

Most preferably, $Ar^2$ is selected from:

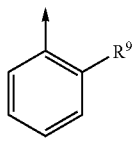

wherein $R^9$ is Cl, Br, I, or $NO_2$; or

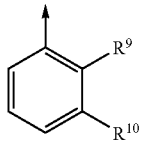

wherein $R^9$ and $R^{10}$ each is F; or wherein $R^9$ and $R^{10}$ each is Cl; or

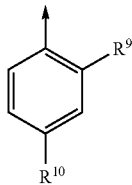

wherein $R^9$ is Cl and $R^{10}$ is OMe, Cl, OH, CN, Ph, C(O)OH or C(O)OMe.

Alternatively, $Ar^2$ is 5-(1, 2, 3, 4-tetrahydronaphthalenyl).

In addition, the method of treatment preferably relates to the compounds of formula 1b wherein $Ar^3$ is

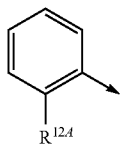

wherein $R^{12A}$ is as defined hereinabove. More preferably, the use of the compounds of formula 1b wherein $Ar^3$ is as defined in the last instance and $R^{12A}$ is a phenyl of formula

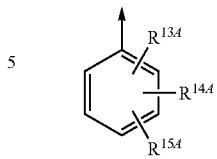

wherein $R^{13A}$, $R^{14A}$, and $R^{15A}$ each independently represents H, Me, Et, Pr, i-Pr, OMe, OEt, SMe, SEt, Br, Cl, F, $CF_3$, $NO_2$, C(O)OH, C(O)OMe or C(O)OEt, provided that at least one of $R^{13A}$, $R^{14A}$, and $R^{15A}$ is other that hydrogen; or $R^{12A}$ is

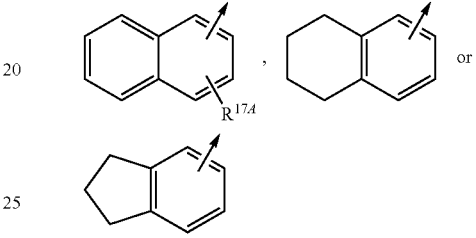

wherein $R^{17A}$ is selected from H, Me, OMe, Cl, F, $CF_3$, $NH_2$, NHMe or $NMe_2$. Most preferably, the use of the compound of formula 1b wherein $Ar^3$ is

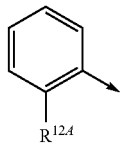

wherein $R^{12A}$ is

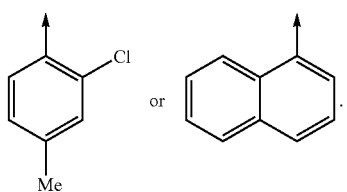

Preferably, $Ar^3$ is

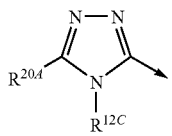

wherein $R^{12C}$ is as defined in the first instance herein, and $R^{20A}$ is H, Me, Et, Pr or iPr. More preferably, the use of the compounds of formula 1b wherein $Ar^3$ is as defined in the last instance and $R^{12C}$ is a phenyl of formula:

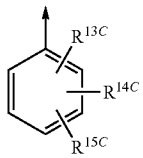

wherein R[13C], R[14C] and R[15C] are respectively as defined above for R[13A], R[14A] and R[15A]; and R[20A] is H, Me or Et; or R[12C] is

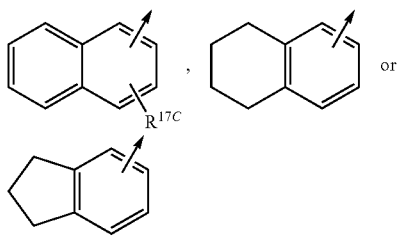

wherein R[17C] is selected from H, Me, OMe, Cl, F, CF$_3$, NH$_2$, NHMe or NMe$_2$; and R[20A] is H, Me or Et. Most preferably, the use of a compound of formula 1b wherein Ar$^3$ is as defined in the last instance and R[12C] is

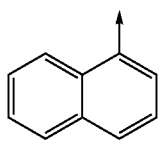

and R[20A] is H or Me.

According to a second embodiment of the first aspect of the present invention there is provided a method for treating HIV infection comprising administering to an infected human a therapeutically effective amount of a compound represented by formula 1a:

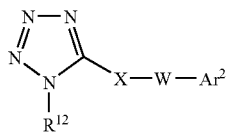

1a wherein X, W and Ar$^2$ are as defined hereinbefore and R[12] is a phenyl of formula

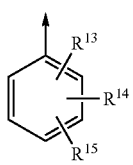

wherein R[13], R[14] and R[15] each independently represents H, (C$_{1-4}$)alkyl, (C$_{3-7}$)cycloalkyl, (C$_{3-7}$)cycloalkyl-(C$_{1-3}$)alkyl, (C$_{2-6}$)alkenyl, O—(C$_{1-4}$)alkyl, S—(C$_{1-4}$)alkyl, halo, CF$_3$, OCF$_3$, OH, NO$_2$, CN, phenyl, 2-methylphenyl, SO$_2$NH$_2$, SO$_2$—(C$_{1-4}$)alkyl, C(O)NH$_2$, morpholino, 1-pyrrolyl, (2-nitrophenyl)-CH$_2$, phenylmethyl, C(O)OR[16] wherein R[16] is H or (C$_{1-4}$)alkyl; or wherein R[12] is selected from the group consisting of

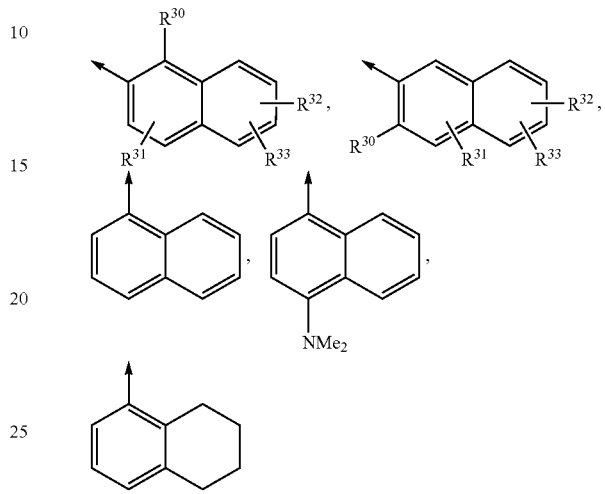

wherein R[31], R[32], R[33] are each independently selected from the group consisting of H, (C$_{1-6}$)alkyl, (C$_{3-7}$)cycloalkyl, (C$_{3-7}$)cycloalkyl-(C$_{1-3}$)alkyl, (C$_{2-6}$)alkenyl, O—(C$_{1-4}$)alkyl, S—(C$_{1-4}$)alkyl, halo, CF$_3$, OCF$_3$, OH, NO$_2$, CN, SO$_2$NH$_2$, SO$_2$—(C$_{1-4}$)alkyl, C(O)OR$^1$ wherein R$^1$ is H or (C$_{1-4}$)alkyl, or NR$^2$R$^3$ wherein R$^2$ and R$^3$ each independently is H or (C$_{1-4}$)alkyl; and
R[30] represents H, Cl, Br, COO(C$_{1-4}$)alkyl.

According to said second embodiment the method of this invention preferably relates to a compound of the formula 1a wherein R[12] is preferably selected from:

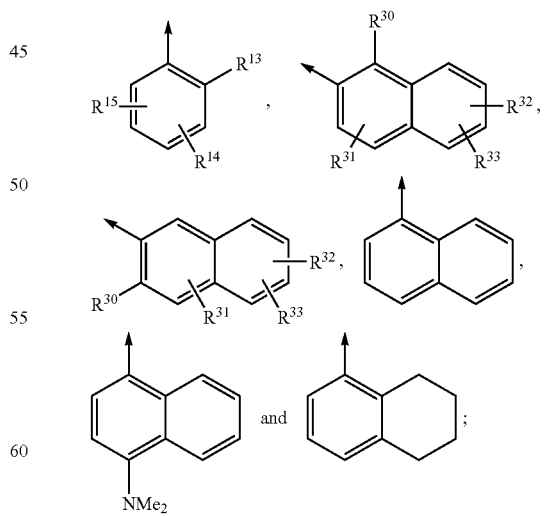

wherein
R[13] represents F, Cl, Br, CH$_3$, COO(C$_{1-4}$)alkyl;
R[14], R[15],

R³¹, R³²,

R³³ are each independently selected from the group consisting of H, (C₁₋₆)alkyl, (C₃₋₇)cycloalkyl, (C₃₋₇)cycloalkyl-(C₁₋₃)alkyl, (C₂₋₆)alkenyl, O—(C₁₋₄)alkyl, S—(C₁₋₄)alkyl, halo, CF₃, OCF₃, OH, NO₂, CN, SO₂NH₂, SO₂—(C₁₋₄)alkyl, C(O)OR¹ wherein R¹ is H or (C₁₋₄)alkyl, or NR²R³ wherein R² and R³ each independently is H or (C₁₋₄)alkyl; and R³⁰ represents H, Cl, Br, COO(C₁₋₄)alkyl.

Most preferably R¹² is selected from the group consisting of:

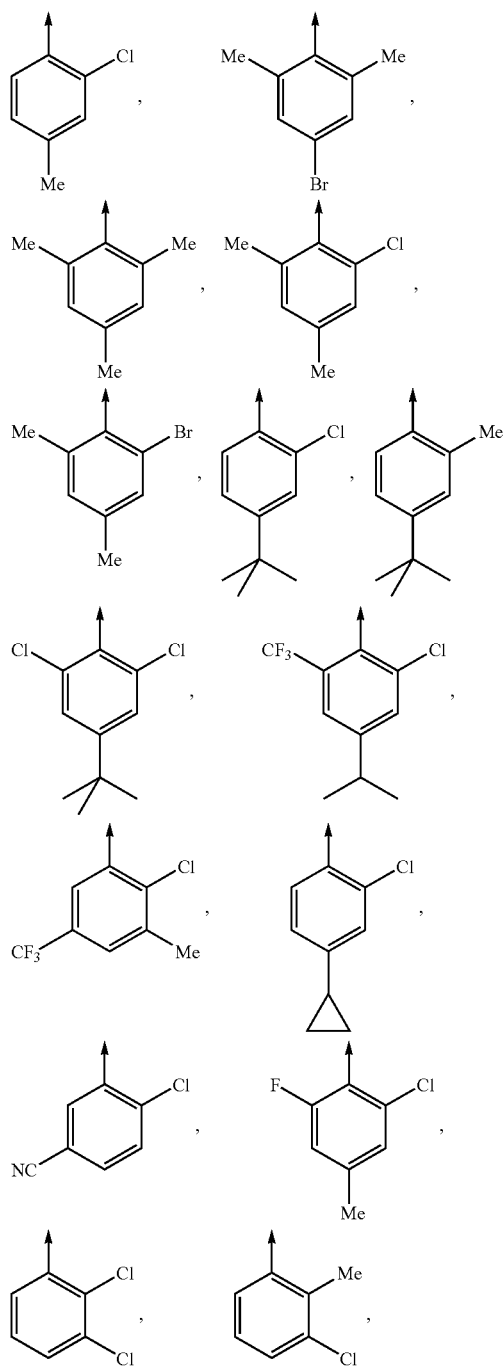

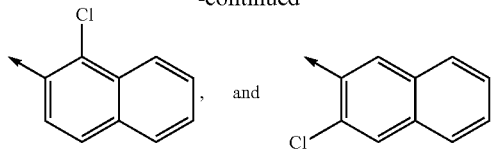

A method according to the present invention is preferred wherein the compound is a compound of formula 1 wherein X is O or S, most preferably S.

Furthermore, a method according to the present invention is preferred wherein the compound is a compound of formula 1 wherein —X—W— is a divalent radical selected from the group consisting of:
 —S—(CR⁵R⁵ᴬ)—CO—NR⁶,
 —O—(CR⁵R⁵ᴬ)—CO—NR⁶,
 —S—(C₂₋₄)alkylene-O—, and
 —S—(C₂₋₄)alkylene-NR⁶ wherein R⁵ and R⁵ᴬ each independently is H or (C₁₋₄)alkyl, R⁶ is H or (C₁₋₄)alkyl; and wherein the (C₂₋₄)alkylene group is optionally substituted with OH.

Most preferably —X—W— is a divalent radical selected from the group consisting of:
 —S—CH₂—CO—NH—,
 —OCH₂—CO—NH—,
 —S—CH₂—CH₂—CHOH—,
 —S—CH₂—CHOH—CH₂—,
 —S—CH₂—CHOH—CH₂—O—, and
 —S—CH₂—CHOH—CH₂—NH—.

A most preferred meaning of the group W is CH(R⁵)C(O)NH wherein R¹⁵ is H or Me.

A method according to the present invention is preferred wherein the compound is a compound of formula 1 wherein Ar² is selected from the group consisting of

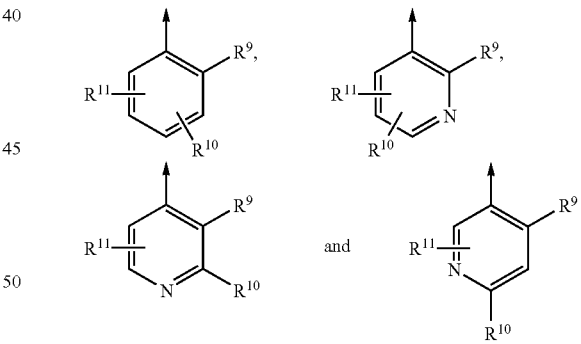

wherein R⁹ is (C₁₋₃)alkyl, halo or NO₂, and
R¹⁰, R¹¹ are independently of each other selected from the group consisting of H, (C₁₋₆)alkyl, (C₃₋₇)cycloalkyl, (C₃₋₇)cycloalkyl-(C₁₋₃)alkyl, (C₂₋₆)alkenyl, O(C₁₋₆)alkyl, S(C₁₋₆)alkyl, halo, CF₃, OCF₃, OH, NO₂, CN, —NRᴺ¹Rᴺ², —C(O)R²¹, —(C₁₋₃)alkyl-C(O)R²¹, —C(O)OR²², —(C₁₋₃)alkyl-C(O)OR²², —SO₂—(C₁₋₃)alkyl-C(O)OR²², —(C₁₋₃)alkyl-C(O)NH₂, C(O)NH₂, —S(O)—(C₁₋₆)alkyl, —SO₂—(C₁₋₆)alkyl, —SO₂-phenyl, —SO₂—NH₂, phenyl, phenylmethyl, 2-, 3- or 4-pyridinyl, 1-pyrrolyl, whereby said phenyl, pyridinyl and pyrrolyl may have one or more substituents selected from the group consisting of halo, NO₂, C₁₋₃-alkyl and CF₃;

wherein $R^{21}$ is $(C_{1-4})$alkyl; $R^{22}$ is H or $(C_{1-4})$alkyl; and wherein $R^{N1}$, $R^{N2}$ each independently represent H or $(C_{1-6})$alkyl, whereby $R^{N1}$ and $R^{N2}$ may be covalently bonded to each other to form together with the N-atom to which they are attached to a 4 to 7-membered heterocycle whereby the —CH$_2$-group at the position 4 of a 6 or 7-membered heterocycle may be replaced by —O—, —S— or —NR$^{N3}$—wherein $R^{N3}$ represents H, —C(O)OR$^{22}$, $(C_{1-6})$alkyl, $(C_{3-7})$cycloalkyl or $(C_{3-7})$cycloalkyl-$(C_{1-3})$alkyl, wherein $R^{22}$ is H or $(C_{1-4})$alkyl.

Most preferably Ar$^2$ is selected from the group consisting of

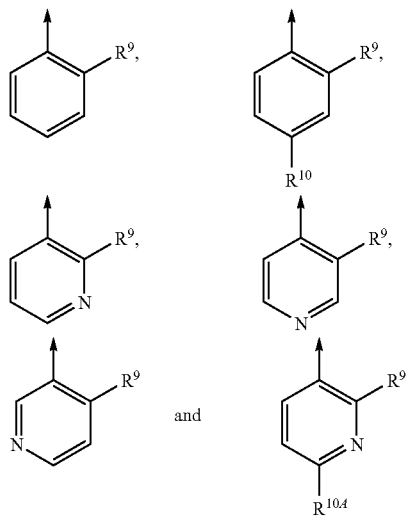

wherein $R^9$ is $C_1$ or NO$_2$;
wherein $R^{10A}$ is $C_{1-4}$alkyl; and
$R^{10}$ is selected from the group consisting of $(C_{1-4})$alkyl, $(C_{3-7})$cycloalkyl, $(C_{3-7})$cycloalkyl-$(C_{1-3})$alkyl, $(C_{2-6})$alkenyl, O$(C_{1-6})$alkyl, S$(C_{1-6})$alkyl, halo, CF$_3$, OCF$_3$, OH, NO$_2$, CN, —NR$^{N1}$R$^{N2}$, —C(O)R$^{21}$, —$(C_{1-3})$alkyl-C(O)R$^{21}$, —C(O)OR$^{22}$, —$(C_{1-3})$alkyl-C(O)OR$^{22}$, —SO$_2$—$(C_{1-3})$alkyl-C(O)OR$^{22}$, —$(C_{1-3})$alkyl-C(O)NH$_2$, C(O)NH$_2$, —S(O)—$(C_{1-6})$alkyl, —SO$_2$—$(C_{1-6})$alkyl, —SO$_2$-phenyl, —SO$_2$—NH$_2$, phenyl, phenylmethyl, phenyl-SO$_2$—, 2-, 3- or 4-pyridinyl, 1-pyrrolyl, whereby said phenyl, pyridinyl and pyrrolyl may have one or more substituents selected from the group consisting of halo, NO$_2$, C$_{1-3}$-alkyl and CF$_3$;

wherein $R^{21}$ is $(C_{1-4})$alkyl; $R^{22}$ is H or $(C_{1-4})$alkyl;

wherein $R^{N1}$, $R^{N2}$ each independently represent H or $(C_{1-6})$alkyl, whereby $R^{N1}$ and $R^{N2}$ may be covalently bonded to each other to form together with the N-atom to which they are attached to a 4 to 7-membered heterocycle whereby the —CH$_2$-group at the position 4 of a 6 or 7-membered heterocycle may be replaced by —O—, —S— or —NR$^{N3}$—wherein $R^{N3}$ represents H, —C(O)OR$^{22}$, $(C_{1-6})$alkyl, $(C_{3-7})$cycloalkyl or $(C_{3-7})$cycloalkyl-$(C_{1-3})$alkyl, wherein $R^{22}$ is H or $(C_{1-4})$alkyl.

In the following preferred embodiments of the second aspect of this invention which is related to new compounds are described.

According to a first embodiment of the second aspect of the present invention, there are provided new compounds of the formula 1

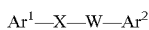     1 wherein Ar$^1$ is

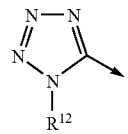

wherein $R^{12}$ is selected from the group consisting of

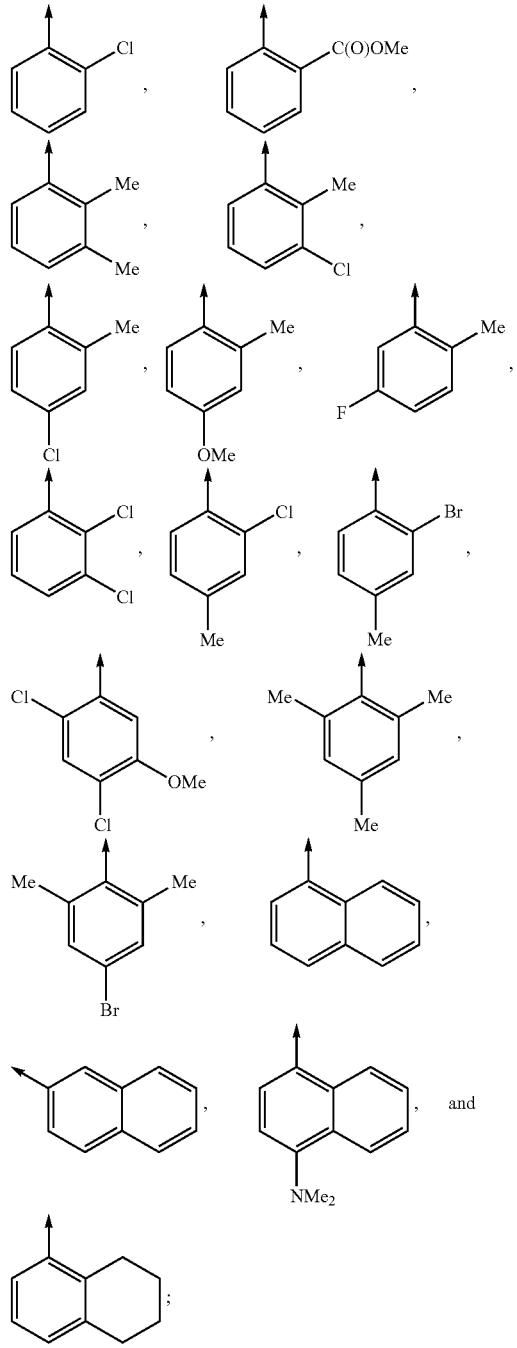

X is S;
W is CH$_2$C(O)NR$^6$ wherein $R^6$ is H or $(C_{1-4})$alkyl; and

Ar² is

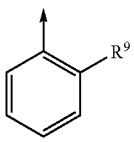

wherein R⁹ is halo or NO₂; or
Ar² is

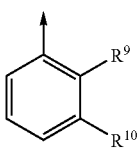

wherein R⁹ is halo or NO₂ and R¹⁰ is halo; or
Ar² is

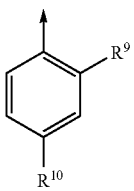

wherein R⁹ is halo or NO₂, and R¹⁰ is OMe, halo, OH, NO₂, phenyl, C(O)OH or C(O)OMe.

Most preferably, new compounds are represented by the formula 1a wherein R¹² is selected from the group consisting of

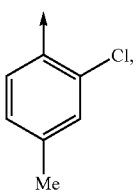 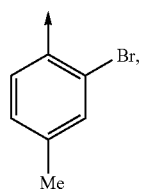

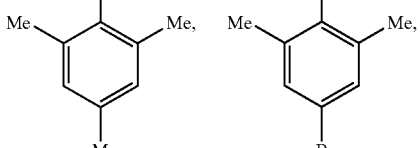 and

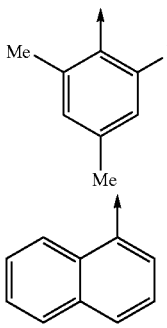

and X, W and Ar² are as defined in the last instance.

Alternatively, according to the first embodiment of the second aspect of the present invention new compounds of the formula 1 are provided Ar¹—X—W—Ar²                1 wherein Ar¹ is

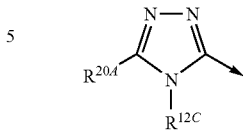

and
wherein R¹²ᶜ is a phenyl of formula

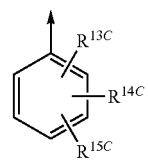

wherein R¹³ᶜ, R¹⁴ᶜ and R¹⁵ᶜ each independently represents H, Me, Et, Pr, iPr, tBu, OMe, OEt, SMe, SEt, Br, Cl, F, CF₃, NO₂, C(O)OH, C(O)OMe or C(O)OEt, provided that at least one of R¹³ᶜ, R¹⁴ᶜ and R¹⁵ᶜ is other than hydrogen; or R¹²ᶜ is

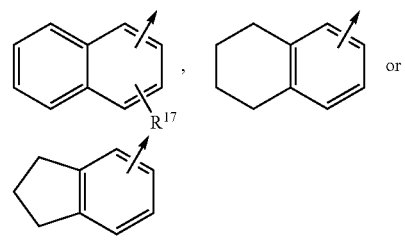

wherein R¹⁷ is selected from H, Me, OMe, Cl, F, CF₃, NH₂, NHMe or NMe₂; and R²⁰ᴬ is H, Me, Et, Pr or iPr.

Most preferably R¹² is selected from the group consisting of:

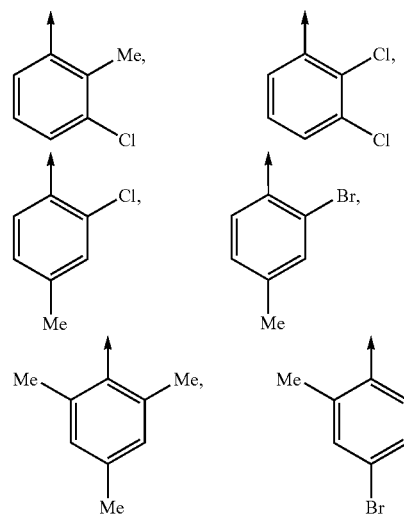

-continued

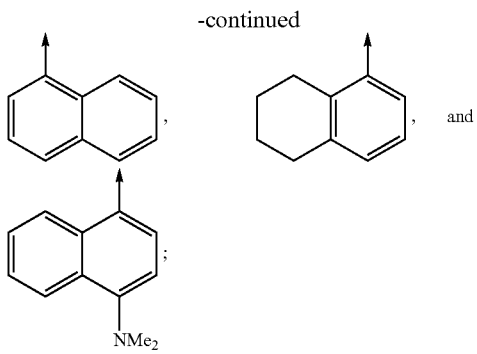

X is S; W is CH$_2$C(O)NH and Ar$^2$ is

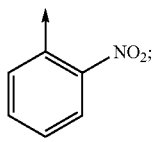

or a compound of formula 1 wherein Ar$^1$ is

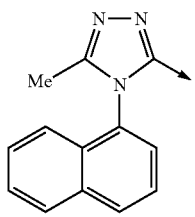

and X, W and Ar$^2$ are as defined in the last instance.

According to a second embodiment of the second aspect of the present invention, there are provided new compounds of the formula 1 wherein Ar$^1$ is

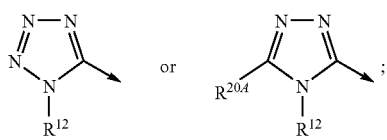

and wherein R$^{12}$ is selected from the group consisting of

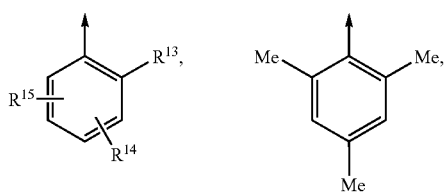

-continued

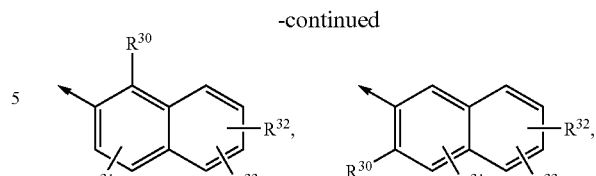

wherein R$^{13}$, R$^{14}$, R$^{15}$, R$^{20A}$, R$^{30}$, R$^{31}$, R$^{32}$ and R$^{33}$ are as defined hereinbefore and hereinafter.

According to this second embodiment preferred meanings of the substituents are:

R$^{13}$ represents Cl or Br; and
if R$^9$ is NO$_2$, Cl or Br, then R$^{13}$ may also represent F or CH$_3$;

R$^{14}$, R$^{15}$,

R$^{31}$, R$^{32}$,

R$^{33}$ are each independently selected from the group consisting of H, (C$_{1-6}$)alkyl, (C$_{3-7}$)cycloalkyl, (C$_{3-7}$)cycloalkyl-(C$_{1-3}$)alkyl, (C$_{2-6}$)alkenyl, O—(C$_{1-4}$)alkyl, S—(C$_{1-4}$)alkyl, halo, CF$_3$, OCF$_3$, OH, NO$_2$, CN, SO$_2$NH$_2$, SO$_2$—(C$_{1-4}$)alkyl, C(O)OR$^1$ wherein R$^1$ is H or (C$_{1-4}$)alkyl, or NR$^2$R$^3$ wherein R$^2$ and R$^3$ each independently is H or (C$_{1-4}$)alkyl; and R$^{30}$ represents Cl or Br.

Most preferably W represents CH$_2$C(O)NH.

Most preferably —X— is —S—.

According to this second embodiment, most preferred are those compounds of the formula 1, wherein Ar$^1$ is:

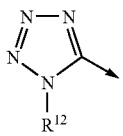

and wherein R$^{12}$ selected from the group consisting of:

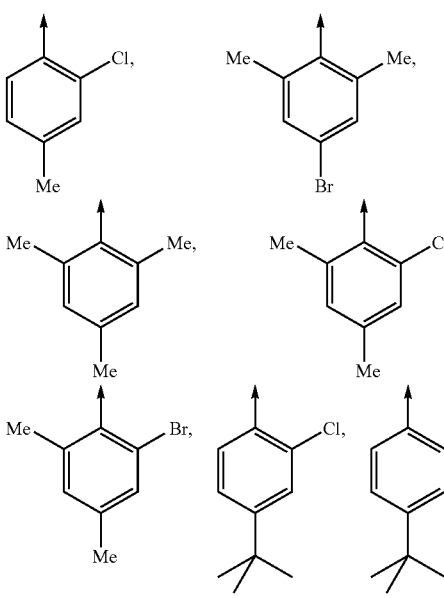

-continued

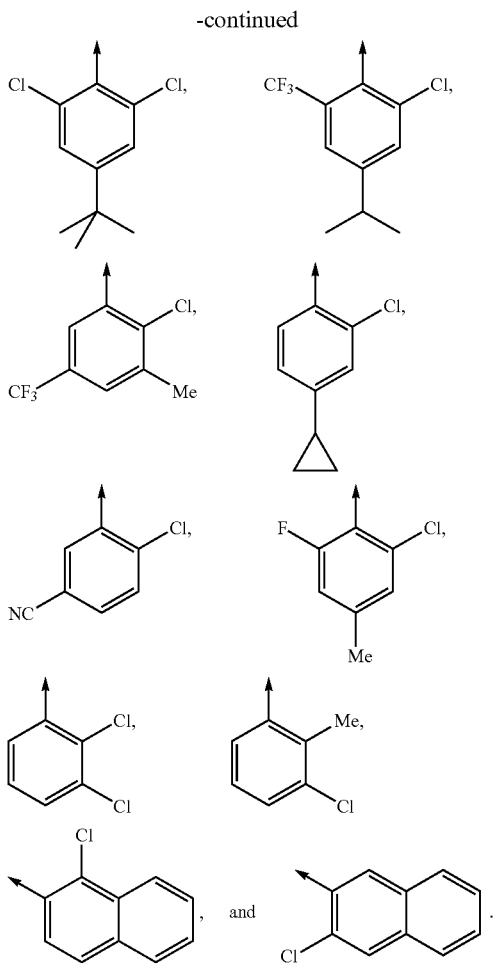

Furthermore, those compounds of formula 1 are preferred wherein Ar¹ is:

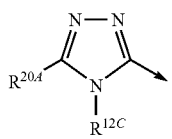

wherein $R^{12C}$ has one of the most preferred meanings of $R^{12}$ as defined above and $R^{20A}$ is H, Me, Et, iPr or 2-hydroxyethyl, preferably $R^{20A}$ is methyl or ethyl.

Furthermore those compounds of the second embodiment of the present invention are preferred wherein Ar² is selected from the group consisting of

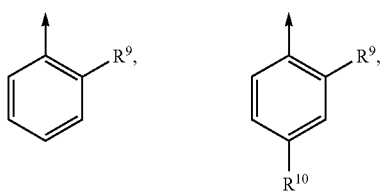

-continued

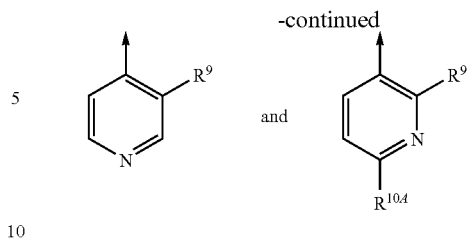

wherein $R^9$ is $C_1$ or $NO_2$ and
$R^{10A}$ is $(C_{1-4})$alkyl;

$R^{10}$ is selected from the group consisting of $(C_{1-4})$alkyl, $(C_{3-7})$cycloalkyl, $(C_{3-7})$cycloalkyl-$(C_{1-3})$alkyl, $(C_{2-6})$alkenyl, $O(C_{1-6})$alkyl, $S(C_{1-6})$alkyl, halo, $CF_3$, $OCF_3$, OH, $NO_2$, CN, —$NR^{N1}R^{N2}$, —C(O)$R^{21}$, —$(C_{1-3})$alkyl-C(O)$R^{21}$, —C(O)$OR^{22}$, —$(C_{1-3})$alkyl-C(O)$OR^{22}$, —$SO_2$—$(C_{1-3})$alkyl-C(O)$OR^{22}$, —$(C_{1-3})$alkyl-C(O)$NH_2$,C(O)$NH_2$, —S(O)—$(C_{1-6})$alkyl, —$SO_2$—$(C_{1-6})$alkyl, —$SO_2$-phenyl, —$SO_2$—$NH_2$, phenyl, phenylmethyl, phenyl-$SO_2$—, 2-, 3- or 4-pyridinyl, 1-pyrrolyl, whereby said phenyl, pyridinyl and pyrrolyl may have one or more substituents selected from the group consisting of halo, $NO_2$, $C_{1-3}$-alkyl and $CF_3$;

wherein $R^{21}$ is $(C_{1-4})$alkyl; $R^{22}$ is H or $(C_{1-4})$alkyl;

wherein $R^{N1}$, $R^{N2}$ each independently represent H or $(C_{1-6})$alkyl, whereby $R^{N1}$ and $R^{N2}$ may be covalently bonded to each other to form together with the N-atom to which they are attached to a 4 to 7-membered heterocycle whereby the —$CH_2$-group at the position 4 of a 6 or 7-membered heterocycle may be replaced by —O—, —S— or —$NR^{N3}$-wherein $R^{N3}$ represents H, —C(O)$OR^{22}$, $(C_{1-6})$alkyl, $(C_{3-7})$cycloalkyl or $(C_{3-7})$cycloalkyl-$(C_{1-3})$alkyl, wherein $R^{22}$ is H or $(C_{1-4})$alkyl.

Most preferably $R^{10}$ is selected from the group consisting of $(C_{1-4})$alkyl, $(C_{3-6})$Cycloalkyl, $CF_3$, OH, —$NH_2$, —COOH, —C(O)$NH_2$, —$SO_2$—$(C_{1-4})$alkyl, —$SO_2$-phenyl, —$SO_2$—$NH_2$, whereby said phenyl may have one or more substituents selected from the group consisting of halo, $NO_2$, $C_{1-3}$-alkyl and $CF_3$.

Most preferably Ar² is selected from the group consisting of:

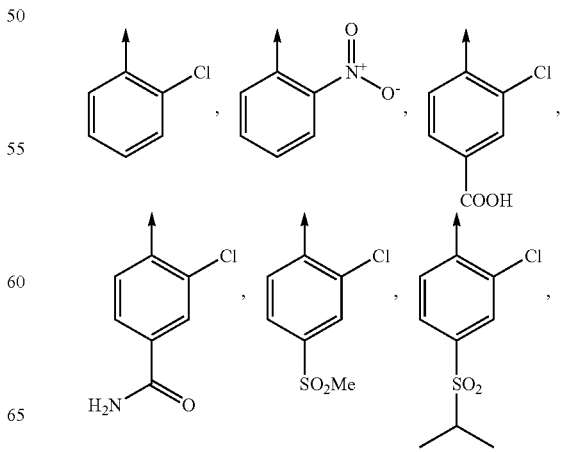

-continued

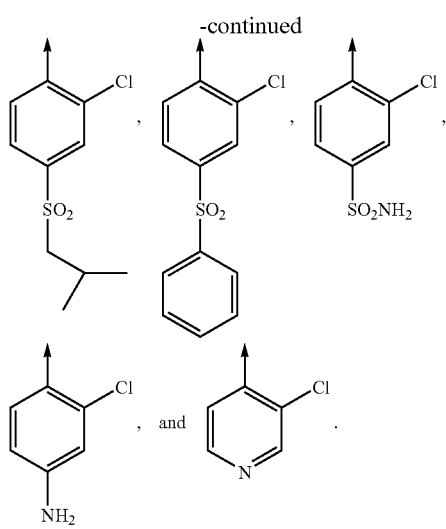

Specific Embodiments

Included within the scope of this invention are all compounds of formula 1 as presented in Tables 1 to 8.

The compounds of formula 1 are effective inhibitors of wild type HIV as well as inhibiting the double mutation enzyme K103N/Y181C. The compounds of the invention may also inhibit the single mutation enzymes V106A, Y188L, K103N, Y181C, P236L and G190A (among others). The compounds may also inhibit other double mutation enzymes including K103N/P225H, K103N/V108I and K103N/L100I.

The compounds of formula 1 possess inhibitory activity against HIV-1 replication. When administered in suitable dosage forms, they are useful in the treatment of AIDS, ARC and related disorders associated with HIV-1 infection. Another aspect of the invention, therefore, is a method for treating HIV-1 infection which comprises administering to a human being, infected by HIV-1, a therapeutically effective amount of a compound of formula 1, as described above. Whether it is termed treatment or prophylaxis, the compounds may also be used to prevent perinatal transmission of HIV-1 from mother to baby, by administration to the mother before giving birth and to the child within the first days of life.

The compounds of formula 1 may be administered in single or divided doses by the oral, parenteral or topical routes. A suitable oral dosage for a compound of formula 1 would be in the range of about 0.5 mg to 3 g per day. A preferred oral dosage for a compound of formula 1 would be in the range of about 100 mg to 800 mg per day for a patient weighing 70 kg. In parenteral formulations, a suitable dosage unit may contain from 0.1 to 250 mg of said compounds, preferably 1 mg to 200 mg, whereas for topical administration, formulations containing 0.01 to 1% active ingredient are preferred. It should be understood, however, that the dosage administration from patient to patient would vary. The dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations that contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The compounds of formula 1 can be used in combination with one or more other antiretroviral drug known to one skilled in the art, as a combined preparation useful for simultaneous, separate or sequential administration for treating or preventing HIV infection in an individual. Examples of antiretroviral drugs that may be used in combination therapy with compounds of formula 1, include but are not limited to, NRTIs (such as AZT), NNRTI's (such as Nevirapine), CCR5 antagonists (such as SCH-351125), CXCR4 antagonists (such as AMD-3100), integrase inhibitors (such as L-870, 810), viral fusion inhibitors (such as T-20), antifungal or antibacterial agents (such as fluconazole), compounds of the TIBO (tetrahydro-imidazo[4,5,1-jk][1,4]-benzodiazepine-2 (1H)-one and thione)-type, compounds of the α-APA (α-anilino phenyl acetamide)-type, TAT inhibitors, protease inhibitors (such as Ritanovir), and immunomodulating agents (such as Levamisole) and investigational drugs (such as DMP-450 or DPC-083). Moreover, a compound of formula 1 can be used with another compound of formula 1.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula 1 can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention may be administerable by suppository.

Methodology and Synthesis

In general, the compounds of formula 1 are prepared by known methods from readily available starting materials, using reaction conditions known to be suitable for the reactants.

A process for preparing a compound of formula 1, wherein X is S or O and W is $(CR^5R^{5A})_{1-2}C(O)NR^6$ as defined herein, is illustrated as follows:

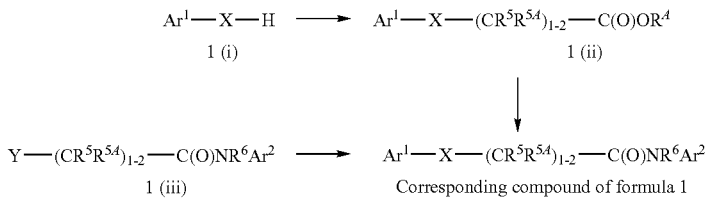

wherein $Ar^1$ and $Ar^2$ are as defined herein, X is S or O, $R^A$ is H or $(C_{1-4})$alkyl and Y is halo, e.g. Br or Cl.

The process comprises:

a) reacting a thiol or alcohol of formula $Ar^1$—X—H {1(i)} with an ω-halo alkanoic alkyl ester of formula Y—$(CR^5R^{5A})_{1-2}C(O)OR^A$ wherein Y is halo and $R^A$ is $(C_{1-4})$alkyl, in the presence of a base, to obtain the corresponding ester of formula $Ar^1$—X—$(CR^5R^5)_{1-2}C(O)OR^A$ {1(ii)}, followed by hydrolysis of the ester to the corresponding acid wherein $R^A$=H, and coupling the latter acid with an aromatic amine of general formula $HNR^6$—$Ar^2$ in the presence of a coupling agent to obtain the corresponding compound of formula 1 wherein $Ar^1$ and $Ar^2$ are as defined herein, X is S or O and W is $(CR^5R^{5A})_{1-2}C(O)$—$NR^6$ as defined herein; or b) reacting a thiol or alcohol of formula $Ar^1$—X—H wherein $Ar^1$ is as defined herein and X is S or O with an anilide of formula Y—$(CR^5R^{5A})_{1-2}C(O)NR^6$—$Ar^2$ in the presence of a base to obtain the corresponding compound of formula 1.

The requisite starting material of formula $Ar^1$—X—H can be prepared readily by reacting a commercially available aromatic isocyanate or isothiocyanates with sodium azide to give directly the desired starting material. The aromatic amine $HNR^6$—$Ar^2$ is either available commercially or can be prepared by known methods.

The requisite aromatic amide of formula Y—$(CR^5R^{5A})_{1-2}$—$C(O)NR^6$—$Ar^2$ can be prepared readily by known methods from commercially available amines; for example, see example 2 hereinafter.

Although several well known coupling agents can be used in the preceding process, phosphorus oxychloride has been found to be practical and efficient.

Processes and reactants for preparing other compounds of formula 1 are illustrated further by the examples hereinafter.

EXAMPLES

The present invention is illustrated in further detail by the following non-limiting examples. All reactions were performed in a nitrogen or argon atmosphere unless otherwise stated. Room temperature is 18 to 22° C. (degrees Celsius). Solution percentages or ratios express a volume to volume relationship, unless stated otherwise.

Abbreviations or symbols used herein include:
Boc: tert-butoxycarbonyl;
CHAPS: 3{(3-cholamidopropyl)dimethylammonio}-1-propanesulfonate;
DEAD: diethyl azodicarboxylate;
DIAD: diisopropyl azodicarboxylate;
DMF: N,N-dimethylformamide;
DMSO: dimethylsulfoxide;
dppf: 1,1'-bis(diphenylphosphino)ferrocene;
DPPBE: 4-diphenylphosphanylbenzoic acid, 2-(trimethylsilyl)ethyl ester;
DTT: DL-dithiothreitol;
$Et_2O$: diethyl ether;
EtOAc: ethyl acetate;
GSH: glutathione;
HPLC: high performance liquid chromatography;
iPr: isopropyl;
LDA: Lithium diisopropylamide;
MCPBA: meta-chloroperbenzoic acid;
Me: methyl;
MeOH: methanol;
MeCN: acetonitrile;
Ph: phenyl;
TBAF: tetrabutylammonium fluoride;
TFA: trifluoroacetic acid;
THF: tetrahydrofuran;

Syntheses

The following examples illustrate methods for preparing compounds of the invention.

Example 1

Entry 208

N-(2-Chlorophenyl)-2-{{1-(1-naphthalenyl)-1H-tetrazol-5-yl}thio}acetamide

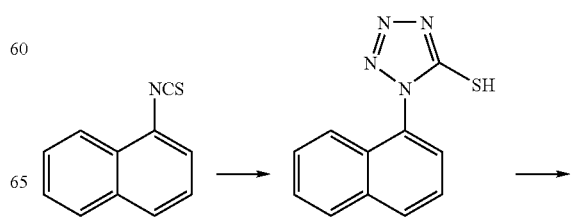

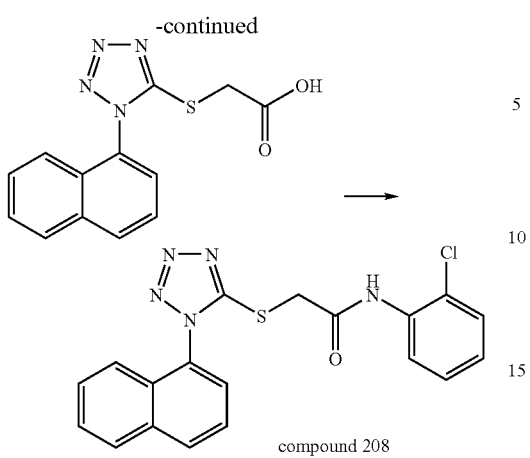

compound 208 a) 1,2-Dihydro-1-(1-naphthalenyl)-5H-tetrazole-5-thione

To a solution of NaN$_3$ (1.76 g, 27.0 mmol) in a mixture of 1,4-dioxane (25 mL) and water (25 mL) was added 1-naphthalenylisothiocyanate (5.00 g, 27.0 mmol) at room temperature. The yellow solution containing a white solid was heated at 102° C. for 2 h. The reaction mixture was then cooled to room temperature and aqueous 1 N HCl solution was added until pH 2 was reached. The aqueous mixture was extracted with EtOAc (250 mL). The organic layer was extracted with aqueous 1 N NaOH solution. The aqueous layer was acidified with aqueous 6 N HCl solution and a white precipitate formed. The suspension was filtered and the resulting solid was triturated with Et$_2$O/hexane (1/1) to give the title compound (3.89 g, 63% yield) as an off white solid.

b) 2-{{1-(1-Naphthalenyl)-1H-tetrazol-5-yl}thio}acetic acid

Pyridine (0.83 mL, 10.3 mmol) and 1,2-dihydro-1-(1-naphthalenyl)-5H-tetrazole-5-thione (2.14 g, 9.38 mmol) were added to a solution of methyl 2-bromoacetate (977 µL, 10.3 mmol) in DMSO (50 mL). The resulting light yellow solution was stirred at room temperature for 2 h. The reaction mixture was then diluted with EtOAc (300 ml) and was successively washed with water (2×250 ml) and brine (100 ml), dried (MgSO$_4$), filtered and concentrated under reduced pressure. The crude ester was dissolved in THF and aqueous 1 N NaOH solution was added. The solution was stirred at room temperature for 30 min. The THF was evaporated under reduced pressure and the residue was dissolved in aqueous 1 N NaOH solution. The solution was slowly acidified to pH 2 at 0° C. with aqueous 1 N HCl solution. The suspension was filtered and the resulting solid was rinsed with water and dried under reduced pressure to give the title compound (2.48 g, 92% yield) as a white solid.

c) N-(2-Chlorophenyl)-2-{{1-(1-naphthalenyl)-1H-tetrazol-5-yl}thio}acetamide 2-{{1-(1-Naphthalenyl)-1H-tetrazol-5-yl}thio}acetic acid (500 mg, 1.75 mmol) and 2-chloroaniline (202 µL, 1.92 mmol) were dissolved in dry pyridine (8 mL). This solution was cooled to 0° C. and POCl$_3$ (0.179 mL) was added dropwise. The mixture was stirred at 0° C. for 1 h, quenched with a few drops of water, and concentrated under reduced pressure. The crude product was dissolved in CH$_2$Cl$_2$ (100 mL) and the resulting solution was successively washed with water (2×30 ml) and brine (30 ml), dried (MgSO$_4$), filtered and concentrated under reduced pressure. The crude product was purified by flash column chromatography (CH$_2$Cl$_2$:(CH$_3$)$_2$CO, 95:5) to afford the title compound (643 mg, 85% yield) as a solid.

Example 2

Entry 101

2-{{1-(1-Naphthalenyl)-1H-tetrazol-5-yl}thio}-N-(2-nitrophenyl)acetamide compound 101 a) 2-Bromo-N-(2-nitrophenyl)acetamide

2-Bromoacetyl bromide (173 µL, 1.99 mmol) was added dropwise to a solution of 2-nitroaniline (250 mg, 1.81 mmol) and pyridine (293 µL) in CH$_2$Cl$_2$ (9 mL). The reaction mixture was stirred at room temperature for 45 min. The mixture was then diluted with CH$_2$Cl$_2$ (10 mL), washed with aqueous 1 N HCl solution (10 mL), water (10 ml) and brine (10 mL). The organic layer was dried (Na$_2$SO$_4$), filtered and concentrated under reduced pressure to yield the title compound (431 mg, 92% yield) as an orange solid.

b) 2-{1-(1-Naphthalenyl)-1H-tetrazol-5-yl}thio)-N-(2-nitrophenyl)acetamide

To a solution of 2-bromo-N-(2-nitrophenyl)acetamide (186 mg, 0.718 mmol) in DMSO (4 mL) was added pyridine (116 µL, 1.43 mmol) followed by 1,2-dihydro-1-(1-naphthalenyl)-5H-tetrazole-5-thione (164 mg, 0.718 mmol). The dark brown solution was stirred at room temperature for 16 h. The reaction mixture was then diluted with CH$_2$Cl$_2$ (40 mL) and washed with water (2×40 mL), brine, dried (Na$_2$SO$_4$), filtered and directly loaded onto silica gel. The crude sample was purified by flash chromatography (EtOAc) to afford 140 mg of a light yellow solid which was lyophilized from water-MeCN to afford (136 mg, 47% yield) of the title compound.

Example 3

Entry 304

1-(1-Naphthalenyl)-N-(2-nitrophenyl)-1H-tetrazole-5-propanamide

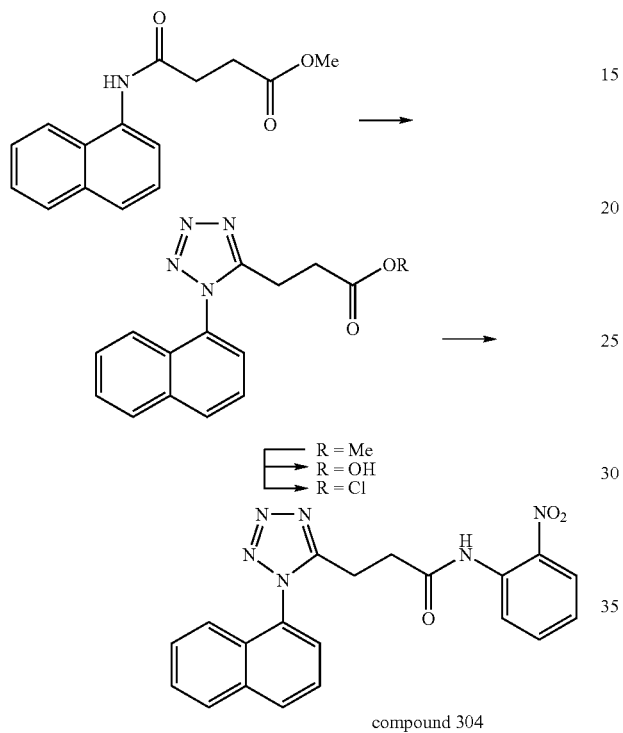

compound 304 a) 1-(1-Naphthalenyl)-1H-tetrazole-5-propanoic acid

A 0.5 M DPPBE solution in THF (20.0 mL, 10.0 mmol), DIAD (1.97 mL, 10.0 mmol) and TMSN$_3$ (1.33 mL, 10.0 mmol) were successively added to a solution of methyl 4-{(1-naphthalenyl)amino}4-oxobutanoate (1.29 g, 5.00 mmol) in THF (30 mL). The reaction mixture was stirred at room temperature for 3 days. A 1.0 M TBAF solution in THF (5.00 mL, 5.00 mmol; additional 5.00 mL added after 5.5 h) was added and the mixture was stirred at room temperature for 6.5 h. The mixture was concentrated under reduced pressure and the residue was taken in EtOAc (250 mL). The solution was successively washed with aqueous 1 N HCl solution (25 mL), water (25 mL), aqueous 1 N NaOH solution (2×15 mL), water (15 mL) and brine (15 mL), dried (MgSO$_4$), filtered and concentrated under reduced pressure. The residue was partially purified by flash chromatography (hexane:EtOAc:CH$_2$Cl$_2$, 3:1:1) to yield the impure ester. The ester was dissolved in THF (10 mL) and MeOH (5 mL) and aqueous 1 N NaOH solution (3.0 mL, 3.00 mmol) was added to the solution. The mixture was heated at 60° C. for 1 h. The organic solvents were removed under reduced pressure. The resulting aqueous solution was washed with EtOAc (2×25 mL). The aqueous layer was rendered acidic by addition of aqueous 1 N HCl solution (15 mL) and was extracted with EtOAc (50 mL). The organic layer was washed with water and brine, dried (MgSO$_4$), filtered and concentrated under reduced pressure to give the title compound (768 mg, 58% yield) as a white solid.

b) 1-(1-Naphthalenyl)-1H-tetrazole-5-propanoyl chloride

A solution of (COCl)$_2$ (310 µL, 3.45 mmol) in CH$_2$Cl$_2$ (1 mL) was added dropwise to a suspension of 1-(1-naphthalenyl)-1H-tetrazole-5-propanoic acid (738 mg, 2.75 mmol) in CH$_2$Cl$_2$ (50 mL) and DMF (50 µL). The reaction mixture was stirred at room temperature for 1.5 h. The mixture was concentrated to give the title compound (789 mg, 100% yield).

c) 1-(1-Naphthalenyl)-N-(2-nitrophenyl)-1H-tetrazole-5-propanamide

A solution of 1-(1-naphthalenyl)-1H-tetrazole-5-propanoyl chloride (112 mg, 0.39 mmol) in THF (2 mL) was added slowly to a solution of 2-nitroaniline (54.5 mg, 0.39 mmol) and pyridine (79.3 µL, 0.98 mmol) in THF (2 mL) at room temperature. The mixture was stirred at room temperature for 16 h. The mixture was diluted with EtOAc (50 mL). The solution was successively washed with aqueous 1 N HCl solution (10 mL), water (10 mL), aqueous saturated NaHCO$_3$ solution (2×5 mL) and brine (10 mL), dried (MgSO$_4$), filtered and concentrated under reduced pressure. The residue was triturated with Et$_2$O:hexane (1:1) to give, after drying, the title compound (72 mg, 47% yield) as a yellow solid.

Example 4

Entry 316 trans-5-{{{2-(2-Chlorophenyl)cyclopropyl}methyl}thio}-1-(1-naphthalenyl)-1H-tetrazole

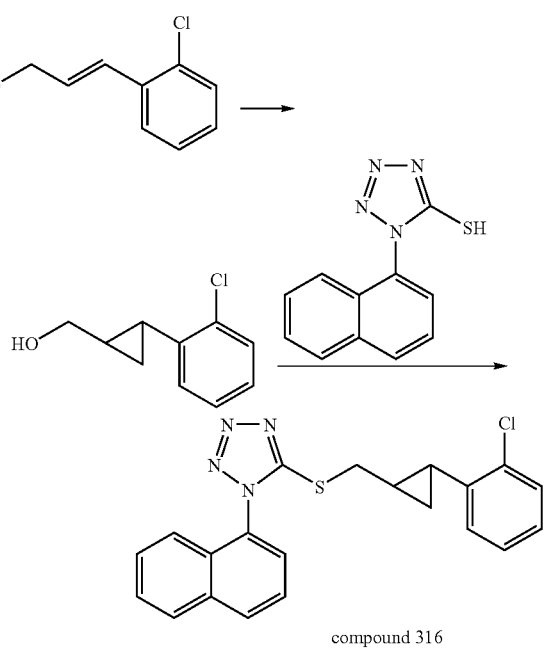

compound 316 a) trans-3-(2-Chlorophenyl)-2-propen-1-ol

A solution of 2-chlorocinnamic acid (5.00 g, 27.4 mmol) in THF (50 mL) was slowly added to a suspension of NaBH₄ (1.24 g, 32.9 mmol) in THF (50 mL) at room temperature. The mixture was stirred until evolution of gas ceased. A solution of I2 (3.47 g, 13.7 mmol) in THF (50 mL) was then added and the mixture was stirred at room temperature for 1 h. Aqueous 3 N HCl solution (10 mL) was added carefully and the mixture was extracted with Et₂O. The combined organic layers were successively washed with aqueous 1 N NaOH solution and brine, dried (MgSO₄), filtered and concentrated under reduced pressure. The residue was purified by flash chromatography (CH₂Cl₂:(CH₃)₂CO, 95:5) to yield the title compound (2.86 g, 62% yield).

b) trans-2-(2-Chlorophenyl)cyclopropanemethanol

Pd(OAc)₂ (13.3 mg, 0.06 mmol) was added to a solution of trans-3-(2-chlorophenyl)-2-propen-1-ol (100 mg, 0.59 mmol) in a solution of CH₂N₂ in Et₂O (ca. 0.6 M, 25 mL). The reaction mixture was stirred at room temperature for 1 h. An additional amount of CH₂N₂ solution in Et₂O (25 mL) was added and the mixture was stirred for 1 h. The mixture was filtered through diatomaceous earth and the filtrate was concentrated under reduced pressure. The residue was purified by flash chromatography (CH₂Cl₂:(CH₃)₂CO, 95:5) to yield the title compound (85.5 mg, 79% yield).

c) trans-5-{{2-(2-Chlorophenyl)cyclopropyl}methyl}thio}-1-(1-naphthalenyl)-1H-tetrazole DIAD (87 μL, 0.44 mmol) was added dropwise to a solution of 1,2-dihydro-1-(1-naphthalenyl)-5H-tetrazole-5-thione (84.0 mg, 0.37 mmol), trans-2-(2-chlorophenyl)cyclopropanemethanol (80.5 mg, 0.44 mmol), and PPh₃ (116 mg, 0.44 mmol) in THF (10 mL) at room temperature. The reaction mixture was stirred at room temperature for 2 h then was concentrated under reduced pressure. The residue was purified by flash chromatography (CH₂Cl₂:(CH₃)₂CO, 95:5) to give the title compound (81 mg, 56% yield) as a white solid.

Example 5

Entry 317

5-{{3-(2-Chlorophenyl)-3-hydroxypropyl}thio}-1-(1-naphthalenyl)-1H-tetrazole

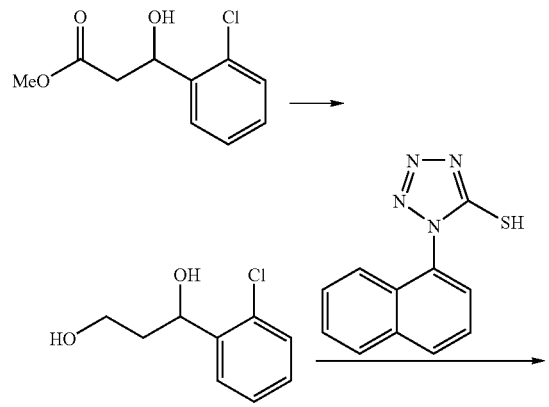

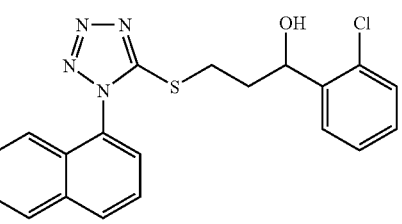

compound 317 a) Methyl 2-chloro-β-hydroxybenzenepropanoate

Methyl acetate (5.09 mL, 64.0 mmol) was added dropwise to a cold (−78° C.) solution of LDA [prepared at 0° C. from i-Pr₂NH (10.5 mL, 74.7 mmol) and 2.0 M n-BuLi in hexane (37.3 mL, 74.7 mmol)] in THF (50 mL). After 45 min, the enolate solution was added via cannula to a cold (−78° C.) solution of 2-chlorobenzaldehyde (3.00 g, 21.3 mmol) in THF (50 mL). The reaction mixture was stirred at −78° C. for 1 h. Aqueous saturated NH₄Cl solution (15 mL) was then added and the mixture was allowed to warm slowly to room temperature. The mixture was concentrated under reduced pressure. The residue was taken in Et₂O (300 mL) and the resulting solution was washed with water (2×50 mL) and brine (50 mL), dried (MgSO₄), filtered and concentrated under reduced pressure. The residue was partially purified by flash chromatography (CH₂Cl₂:(CH₃)₂CO, 95:5) to give the title compound (2.9 g, 63% yield).

b) 1-2-Chlorophenyl)-1,3-propanediol

LiAlH₄ (1.28 g, 33.8 mmol) was added to an ice-cold solution of methyl 2-chloro-β-hydroxybenzenepropanoate (2.90 g, 13.5 mmol) in THF (70 mL). The reaction mixture was stirred at 0° C. for 2 h. Water (4.0 mL), aqueous 10% NaOH solution (4.0 mL) and water (12 mL) were successively added to the mixture. Et₂O (300 mL) was added and the mixture was washed with water (2×100 mL) and brine (100 mL), dried (MgSO₄), filtered and concentrated under reduced pressure. The residue was purified by flash chromatography (hexane:EtOAc, 1:1) to give the title compound (829 mg, 33% yield).

c) 5-{{3-(2-Chlorophenyl)-3-hydroxypropyl}thio}-1-(1-naphthalenyl)-1H-tetrazole DIAD (82 μL, 0.42 mmol) was added dropwise to a solution of 1,2-dihydro-1-(1-naphthalenyl)-5H-tetrazole-5-thione (80.0 mg, 0.35 mmol), 1-(2-chlorophenyl)-1,3-propanediol (65.4 mg, 0.35 mmol), and PPh₃ (110 mg, 0.42 mmol) in THF (10 mL) at room temperature. The reaction mixture was stirred at room temperature for 2 h then was concentrated under reduced pressure. The residue was purified by flash chromatography (CH₂Cl₂:(CH₃)₂CO, 95:5) to give the title compound (70 mg, 50% yield) as a white solid.

Example 6

Entry 318

5-{{3-(2-Chlorophenyl)-2-hydroxypropyl}thio}-1-(1-naphthalenyl)-1H-tetrazole

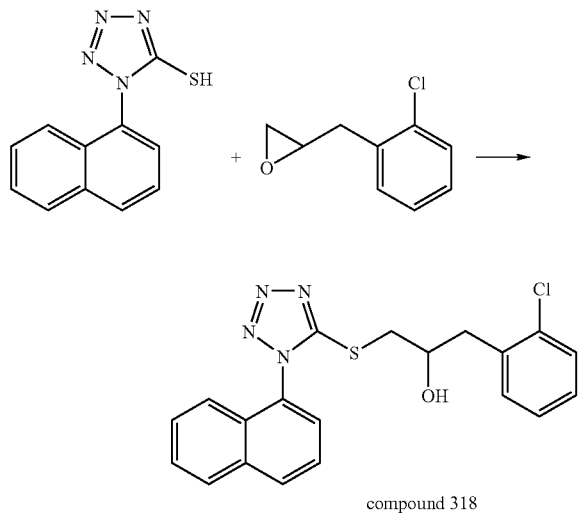

compound 318 a) 2-Chloro-1-(2,3-epoxypropyl)benzene

MCPBA (826 mg, 3.83 mmol) was added portionwise to an ice-cold solution of 2-chloro-1-allylbenzene (487 mg, 3.19 mmol) in $CH_2Cl_2$ (20 mL). The mixture was stirred at room temperature for 16 h. Aqueous 10% $Na_2CO_3$ solution (10 mL) and $CH_2Cl_2$ (100 mL) were added. The solution was successively washed with aqueous 10% $Na_2S_2O_3$ (2×40 mL) and brine (40 mL), dried ($MgSO_4$), filtered and concentrated under reduced pressure. The residue was purified by flash chromatography (hexane:EtOAc, 8:2) to give the title compound (512 mg, 95% yield).

b) 5-{{3-(2-Chlorophenyl)-2-hydroxypropyl}thio}-1-(1-naphthalenyl)-1H-tetrazole

A solution of 1,2-dihydro-1-(1-naphthalenyl)-5H-tetrazole-5-thione (50.0 mg, 0.22 mmol), 2-chloro-1-(2,3-epoxypropyl)benzene (36.9 mg, 0.22 mmol) and $Et_3N$ (0.15 mL, 1.10 mmol) in MeOH (5 mL) was heated at reflux for 2 h. The mixture was concentrated under reduced pressure and the residue was purified by HPLC using a gradient of MeCN/$H_2O$ containing TFA (0.1%) (CombiPrep ODS-AQ 50×20 mm, 5µ, 120 Å). The pure fractions were concentrated to give the title compound (12 mg, 14% yield) as a colorless solid.

Example 7

Entry 330

5-{{3-{(2-Chlorophenyl)amino}-2-hydroxypropyl}thio}-1-(1-naphthalenyl)-1H-tetrazole

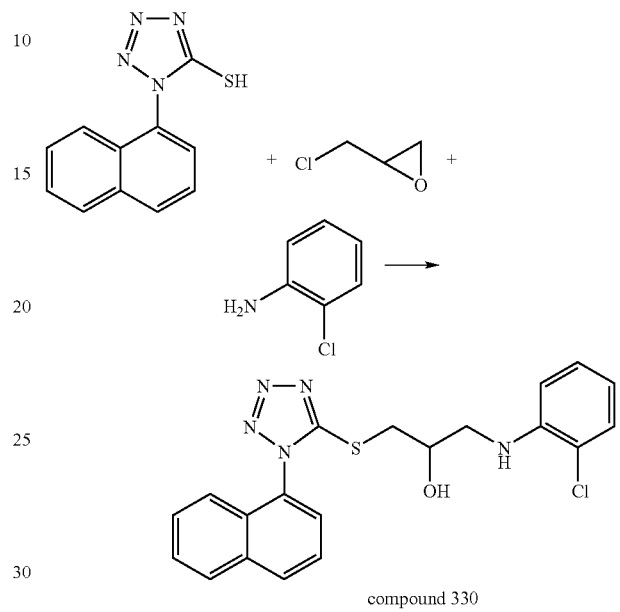

compound 330

A solution of 2-chloroaniline (46.1 µL, 0.44 mmol), epichlorohydrin (51.4 µL, 0.66 mmol) and $Et_3N$ (0.30 mL, 2.19 mmol) in MeOH (10 mL) was heated at reflux for 16 h. The reaction mixture was concentrated under reduced pressure and the residue was purified by flash chromatography. A solution of the intermediate obtained (93.4 mg), 1,2-dihydro-1-(1-naphthalenyl)-5H-tetrazole-5-thione (50.0 mg, 0.22 mmol) and $Et_3N$ (0.30 mL, 2.19 mmol) in MeOH (10 mL) was heated at reflux for 3 days. The mixture was concentrated under reduced pressure and the residue was purified by HPLC using a gradient of MeCN/$H_2O$ containing TFA (0.1%) (CombiPrep ODS-AQ 50×20 mm, 5µ, 120 Å). The pure fractions were concentrated to give the title compound (11.7 mg, 13% yield) as a pale yellow solid.

Example 8

Entry 401

2-{{4-(1-Naphthalenyl)-1H-imidazol-2-yl}thio}-N-(2-nitrophenyl)acetamide

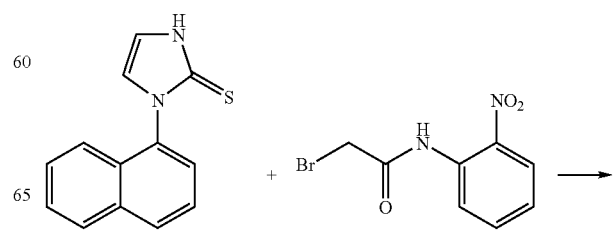

-continued

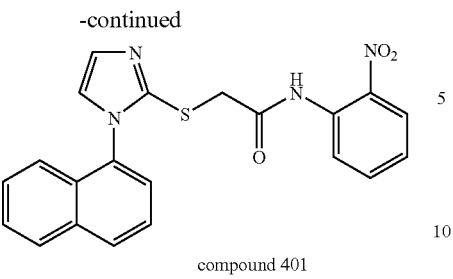

compound 401

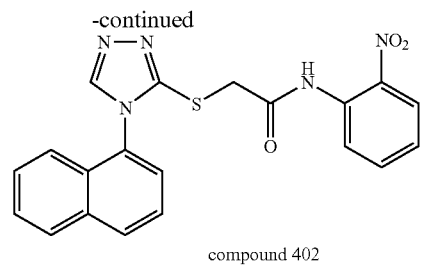

compound 402 a) 1,3-Dihydro-1-(1-naphthalenyl)-2H-imidazole-2-thione

A solution of 1-naphthalenylthioisocyanate (893 mg, 4.82 mmol) and 2-aminoacetaldehyde diethyl acetal (0.70 mL, 4.85 mmol) in toluene (10 mL) was stirred at room temperature for 1 h. Aqueous 12 N HCl solution (0.2 mL) was added and the mixture was heated at 110° C. for 3 h and then stirred at room temperature for 16 h. The mixture was concentrated under reduced pressure. The residue was triturated with hot EtOAc to give the title compound (608 mg, 56% yield).

b) 2-{{4-(1-Naphthalenyl)-1H-imidazol-2-yl}thio}-N-(2-nitrophenyl)acetamide

A solution of 1,3-dihydro-1-(1-naphthalenyl)-2H-imidazole-2-thione (129 mg, 0.50 mmol) in DMSO (2 mL) was added slowly to a solution of 2-bromo-N-(2-nitrophenyl)acetamide (113 mg, 0.50 mmol) and pyridine (121 μL, 1.49 mmol) in DMSO (1 mL) at room temperature. The mixture was stirred at room temperature for 18 h, then diluted with water and extracted with EtOAc (50 mL). The organic layer was washed with water (3×) and brine, dried (MgSO$_4$), filtered and concentrated under reduced pressure. The residue was purified by HPLC using a gradient of MeCN/H$_2$O containing TFA (0.06%) (CombiPrep ODS-AQ 50×20 mm, 5μ, 120 Å). The pure fractions were combined and lyophilized to give the title compound (8.4 mg, 4% yield).

Example 9

Entry 402

2-{{4-(1-Naphthalenyl)-4H-1,2,4-triazol-3-yl}thio}-N-(2-nitrophenyl)acetamide a) 2,4-Dihydro-4-(1-naphthalenyl)-3H-1,2,4-triazole-3-thione A solution of 4-(1-naphthalenyl)-3-thiosemicarbazide (4.01 g, 18.4 mmol) and N,N,-dimethylformamide dimethyl acetal (2.50 mL, 18.8 mmol) in 1,4-dioxane (40 mL) was stirred at room temperature for 16 h. The mixture was concentrated under reduced pressure. The residue was taken in hexane and Et$_2$O and the solution was stirred until a suspension was obtained. The suspension was filtered and the solid was triturated with hexane:Et$_2$O (4:1), then was dried under reduced pressure to give the title compound (4.19 g, 90% yield) as a beige solid.

b) 2-{{4-(1-Naphthalenyl)-4H-1,2,4-triazol-3-yl}thio}-N-(2-nitrophenyl)acetamide A solution of 2,4-dihydro-4-(1-naphthalenyl)-3H-1,2,4-triazole-3-thione (129 mg, 0.50 mmol) in DMSO (2 mL) was added slowly to a solution of 2-bromo-N-(2-nitrophenyl)acetamide (113 mg, 0.50 mmol) and pyridine (121 μL, 1.49 mmol) in DMSO (1 mL) at room temperature. The mixture was stirred at room temperature for 18 h, then diluted with water and extracted with EtOAc (50 mL). The organic layer was washed with water (3×) and brine, dried (MgSO$_4$), filtered and concentrated under reduced pressure. A mixture of Et$_2$O and hexane (1:1) was added, the resulting suspension was filtered and the filtrate was concentrated under reduced pressure. The residue was purified by HPLC using a gradient of MeCN/H$_2$O containing TFA (0.06%) (CombiPrep ODS-AQ 50×20 mm, 5μ, 120 Å). The pure fractions were combined and concentrated to give the title compound (4.5 mg, 2% yield).

Example 10

Entry 406

2-{{2-(1-Naphthalenyl)phenyl}thi}-N-(2-chorophenyl)acetamid

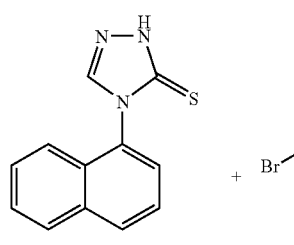 + 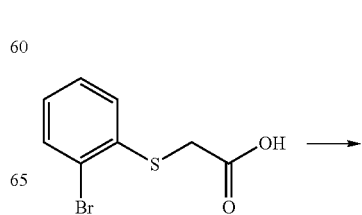 →

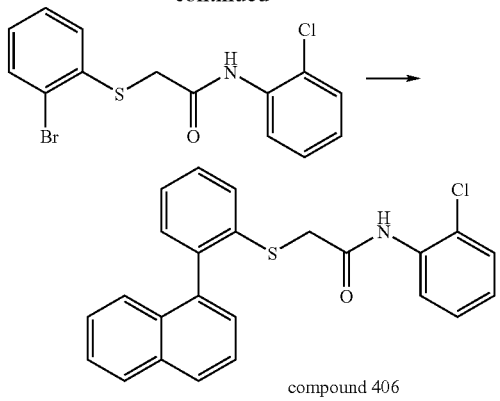

compound 406 a) 2-{(2-Bromophenyl)thio}acetic acid

2-Bromothiophenol (4.00 g, 21.6 mmol) was added to a solution of methyl 2-bromoacetate (2.20 mL, 23.3 mmol) and pyridine (1.88 mL, 23.3 mmol) in DMSO (50 mL) at room temperature. The reaction mixture was stirred at room temperature for 1 h. The mixture was diluted with EtOAc (300 mL) and the resulting solution was washed with water (2×250 mL) and brine (100 mL), dried (MgSO$_4$), filtered and concentrated under reduced pressure. The residue was dissolved in THF (50 mL), aqueous 1 N NaOH solution (25 mL, 25 mmol) was added and the mixture was stirred at room temperature for 45 min. The mixture was concentrated and the aqueous solution was diluted with aqueous 1 N NaOH solution. The solution was cooled to 0° C. and was slowly rendered acidic (pH=2) by addition of aqueous 1 N HCl solution. The resulting suspension was filtered, the solid was washed with water and dried under reduced pressure to give the title compound (3.71 g, 71% yield) as a white solid.

b) 2-{(2-Bromophenyl)thio}-N-(2-chlorophenyl)acetamide

PCl$_3$ (0.39 mL, 4.45 mmol) was added to an ice-cold solution of 2-{(2-bromophenyl)thio}acetic acid (1.00 g, 4.05 mmol) and 2-chloroaniline (0.47 mL, 4.45 mmol) in pyridine (15 mL). The reaction mixture was stirred at room temperature for 30 min. Water (few drops) was added and the mixture was concentrated under reduced pressure. The residue was purified by flash chromatography (CH$_2$Cl$_2$) to give the title compound (957 mg, 66% yield) as a yellow solid.

c) 2-{{2-(1-Naphthalenyl)phenyl}thio}-N-(2-chorophenyl)acetamide

PdCl$_2$(dppf) (1:1 complex with CH$_2$Cl$_2$, 41.0 mg, 56.0 μmol) and dppf (31.1 mg, 56.1 μmol) were added to a degassed (N$_2$, 45 min) solution of 2-{2-bromophenyl)thio}-N-(2-chlorophenyl)acetamide (200 mg, 0.56 mmol), 1-naphthaleneboronic acid (116 mg, 0.67 mmol) and K$_3$PO$_4$ (357 mg, 1.68 mmol) in 1,4-dioxane (5 mL). The reaction mixture was heated at 100° C. for 3 h. The cooled mixture was diluted with EtOAc (50 mL) and filtered. The filtrate was concentrated under reduced pressure. The residue was purified by flash chromatography (CH$_2$Cl$_2$:(CH$_3$)$_2$CO, 98:2) to give the title compound (147 mg, 65% yield) as a pale orange solid.

Tables 1 to 8 illustrate further compounds of the present invention, which can be synthesized in analogy to the methods as described hereinbefore, optionally modified by procedures known to the one skilled in the art.

TABLE 1

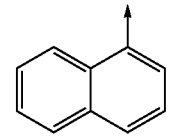

| Entry # | R$^{12}$ | MS ES$^+$ (MH) |
|---|---|---|
| 101 | 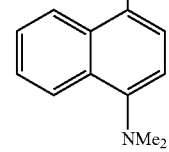 | 407 |
| 102 | 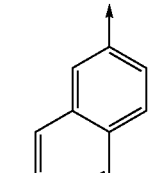 | 450 |
| 103 | 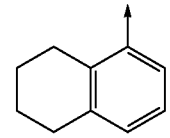 | 407 |
| 104 | 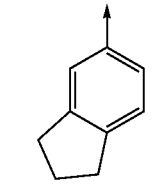 | 411 |
| 105 | 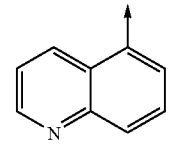 | 397 |
| 106 | 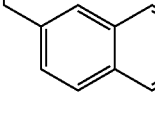 | 408 |
| 107 | 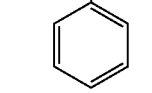 | 421 |
| 108 |  | 357 |

TABLE 1-continued
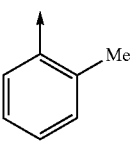
| Entry # | R[12] | MS ES+ (MH) |
|---|---|---|
| 109 | 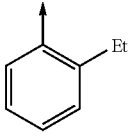 o-Me | 371 |
| 110 | 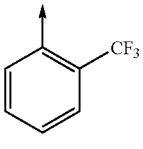 o-Et | 385 |
| 111 | 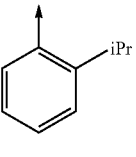 o-CF$_3$ | 425 |
| 112 | 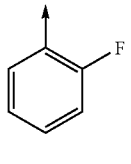 o-iPr | 399 |
| 113 | 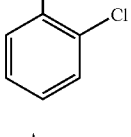 o-F | 375 |
| 114 | 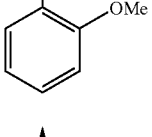 o-Cl | 391/393 |
| 115 | 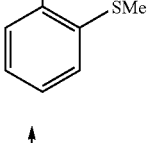 o-OMe | 387 |
| 116 | 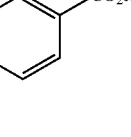 o-SMe | 403 |
| 117 | 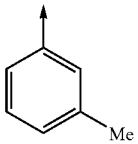 o-CO$_2$Me | 415 |
TABLE 1-continued
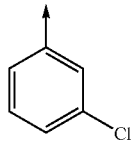
| Entry # | R[12] | MS ES+ (MH) |
|---|---|---|
| 118 | 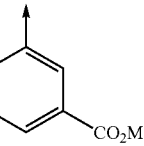 m-Me | 371 |
| 119 | 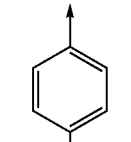 m-Cl | 391/393 |
| 120 | 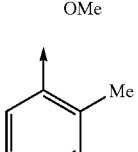 m-CO$_2$Me | 415 |
| 121 | 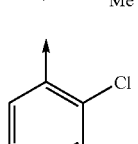 p-OMe | 387 |
| 122 | 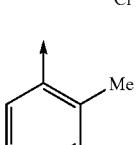 2,3-diMe | 385 |
| 123 | 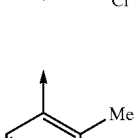 2,3-diCl | 425/427/429 |
| 124 | 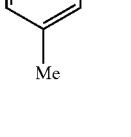 2-Me-3-Cl | 405/407 |
| 125 | 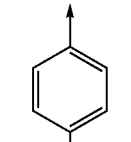 2,4-diMe | 385 |

TABLE 1-continued
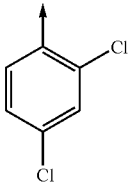
| Entry # | R^{12} | MS ES⁺ (MH) |
|---|---|---|
| 126 | 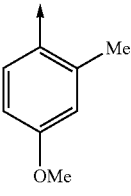 | 425/427/429 |
| 127 | 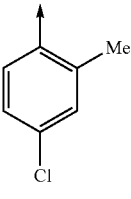 | 401 |
| 128 | 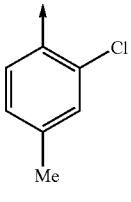 | 405/407 |
| 129 | 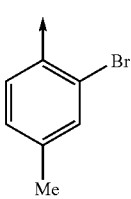 | 405/407 |
| 130 | 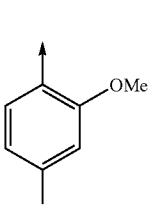 | 449/451 |
| 131 | 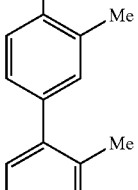 | 417 |
| 132 | 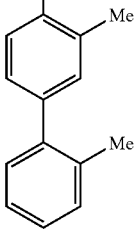 | 461 |
| 133 | 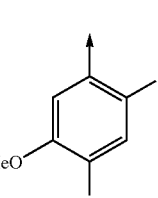 | 455/457/459 |
| 134 | 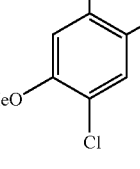 | 483/485/487 |
| 135 | 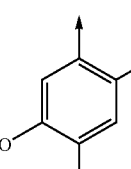 | 387 MS ES⁺ (M − H) |
| 136 | 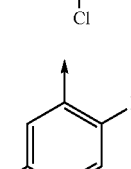 | 421/423 |
| 137 | 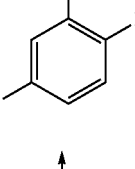 | 457/459 MS ES⁺ (M − H) |
| 138 | 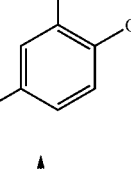 | 385 |

TABLE 1-continued

Structure: 1-R12-tetrazol-5-yl-S-CH2-C(=O)-NH-(2-nitrophenyl)

| Entry # | R12 | MS ES+ (MH) |
|---|---|---|
| 139 | 2-Cl-6-Me-phenyl | 405/407 |
| 140 | 2,6-diMe-4-Br-phenyl | 461/463 MS ES+ (M − H) |
| 141 | 2,4,6-triMe-phenyl | 399 |
| 142 | 4-iPr-phenyl | 399 |
| 143 | 4-NEt2-phenyl | 428 |
| 144 | 2,6-diCl-phenyl | 425/427/429 |
| 145 | 2-Cl-5-Me-phenyl | 405/407 |
| 146 | 2-Me-6-Cl-4-Me-phenyl | 419/421 |
| 147 | 2-Me-6-Br-4-Me-phenyl | 463/465 |

TABLE 2

Structure: 1-(naphthalen-1-yl)-tetrazol-5-yl-S-CH2-C(=O)-NH-Ar2

| Entry # | Ar2 | MS ES+ (MH) |
|---|---|---|
| 201 | phenyl | 362 |
| 202 | 2-Me-phenyl | 376 |
| 203 | 2-Et-phenyl | 390 |
| 204 | 2-iPr-phenyl | 404 |
| 205 | 2-PhCH2-phenyl | 452 |

TABLE 2-continued

[Structure: 1-naphthyl-tetrazole-S-CH2-C(=O)-NH-Ar2]

| Entry # | Ar² | MS ES⁺ (MH) |
|---|---|---|
| 206 | 2-Ph-C6H4 | 438 |
| 207 | 2-F-C6H4 | 380 |
| 208 | 2-Cl-C6H4 | 396/398 |
| 209 | 2-Br-C6H4 | 440/442 |
| 210 | 2-I-C6H4 | 488 |
| 211 | 2-HO-C6H4 | 378 |
| 212 | 2-MeO-C6H4 | 392 |
| 213 | 2-EtO-C6H4 | 406 |
| 214 | 2-CF3-C6H4 | 430 |
| 215 | 2-MeC(O)-C6H4 | 404 |
| 216 | 2-MeO2C-C6H4 | 420 |
| 217 | 2-H2NC(O)-C6H4 | 405 |
| 218 | 2-MeS-C6H4 | 408 |
| 219 | 2-MeSO2-C6H4 | 440 |
| 220 | 2-NH2SO2-C6H4 | 441 |
| 221 | 2-morpholino-C6H4 | 447 |
| 222 | 2-(1-pyrrolyl)-C6H4 | 427 |
| 223 | 3-NO2-C6H4 | 407 |
| 224 | 4-MeO-C6H4 | 392 |
| 225 | 4-HO-C6H4 | 378 |
| 226 | 4-Ph-C6H4 | 438 |

TABLE 2-continued
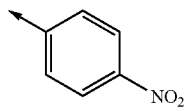
| Entry # | Ar² | MS ES⁺ (MH) |
|---|---|---|
| 227 | 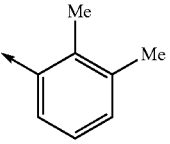 | 407 |
| 228 | 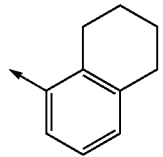 | 390 |
| 229 | 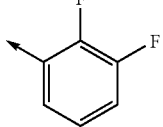 | 416 |
| 230 | 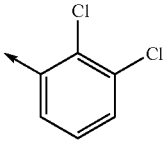 | 398 |
| 231 | 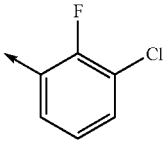 | 430/432/434 |
| 232 | 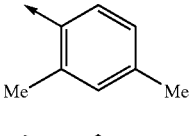 | 414/416 |
| 233 | 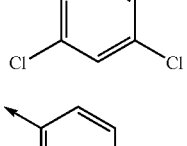 | 390 |
| 234 | 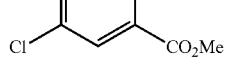 | 430/432/434 |
| 235 | 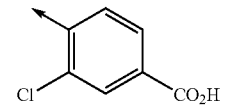 | 454/456 |
TABLE 2-continued
| Entry # | Ar² | MS ES⁺ (MH) |
|---|---|---|
| 236 | 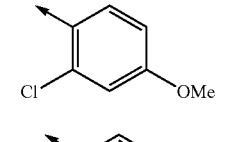 | 440/442 |
| 237 | 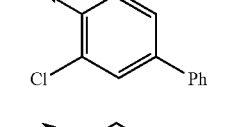 | 426/428 |
| 238 | 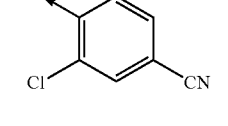 | 472/474 |
| 239 | 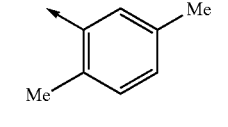 | 419 MS ES⁺ (M − H) |
| 240 | 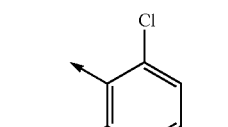 | 390 |
| 241 | 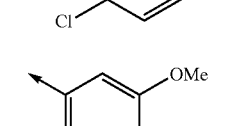 | 430/432/434 |
| 242 | 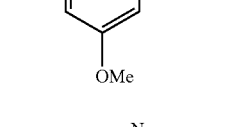 | 422 |
| 243 | 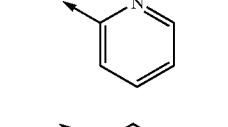 | 363 |
| 244 | | 363 |
| 245 | 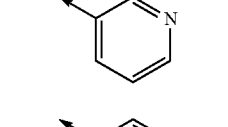 | 363 |

TABLE 2-continued

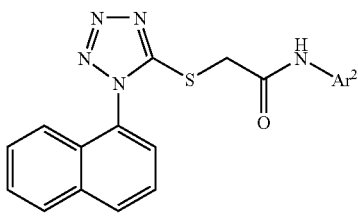

| Entry # | Ar² | MS ES⁺ (MH) |
|---|---|---|
| 246 | 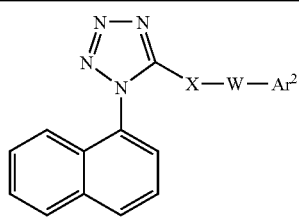 | 412/414 |

TABLE 3

| Entry # | X | W | Ar² | MS ES⁺ (MH) |
|---|---|---|---|---|
| 301 | S | CHMeC(O)NH | 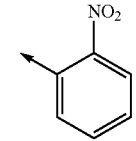 o-NO₂-phenyl | 421 |
| 302 | O | CH₂C(O)NH | o-NO₂-phenyl | 391 |
| 303 | NH | CH₂C(O)NH | o-NO₂-phenyl | 390 |
| 304 | CH₂ | CH₂C(O)NH | o-NO₂-phenyl | 389 |
| 305 | CH₂ | CH₂CH₂C(O)NH | o-Cl-phenyl | 392/394 |

TABLE 3-continued

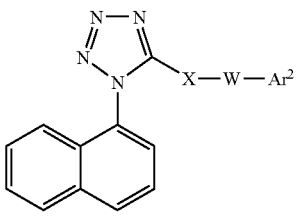

| Entry # | X | W | Ar² | MS ES⁺ (MH) |
|---|---|---|---|---|
| 306 | CH₂ | CH₂CH₂C(O)NH | o-NO₂-phenyl | 403 |
| 307 | CH | CHC(O)NH | o-NO₂-phenyl | 387 |
| 308 | S | CH₂C(S)NH | o-Cl-phenyl | 412/414 |
| 309 | S | CH₂CHOH | o-NO₂-phenyl | 394 |
| 310 | S | CH₂CH₂ | o-NO₂-phenyl | 378 |
| 311 | S | CH₂CH₂CH₂ | o-Cl-phenyl | 381/383 |
| 312 | S | trans-CH₂CH=CH | o-NO₂-phenyl | 390 |
| 313 | S | trans-CH₂CH=CH | o-Cl-phenyl | 379/381 |

TABLE 3-continued

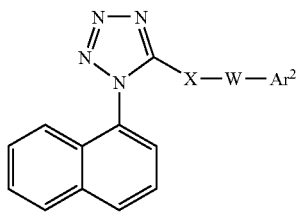

| Entry # | X | W | Ar² | MS ES⁺ (MH) |
|---|---|---|---|---|
| 314 | S | trans-CH₂CF=CH | 2-Cl-phenyl | 397/399 |
| 315 | S | cis-CH₂CF=CH | 2-Cl-phenyl | 397/399 |
| 316 | S | (2-methylcyclopropyl) | 2-Cl-phenyl | 393/395 |
| 317 | S | CH₂CH₂CHOH | 2-Cl-phenyl | 397/399 |
| 318 | S | CH₂CH(OH)CH₂ | 2-Cl-phenyl | 397/399 |
| 319 | S | CH₂CH(OH)CHOH | 2-Cl-phenyl | 413/415 |
| 320 | S | CH₂CH₂O | 2-NO₂-phenyl | 394 |
| 321 | S | CH₂CH₂O | 2-Cl-phenyl | 383/385 |

TABLE 3-continued

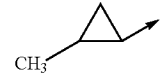

| Entry # | X | W | Ar² | MS ES⁺ (MH) |
|---|---|---|---|---|
| 322 | S | CH₂CH₂O(CO) | 2-NO₂-phenyl | 422 |
| 323 | S | CH₂CH₂O(CO) | 2-Cl-phenyl | 411/413 |
| 324 | S | CH₂CH₂CH₂O | 2-Cl-phenyl | 397/399 |
| 325 | S | CH₂CH(OH)CH₂O | 2-Cl-phenyl | 413/415 |
| 326 | S | CH₂CH₂NH | 2-NO₂-phenyl | 393 |
| 327 | S | CH₂CH₂NMe | 2-NO₂-phenyl | 407 |
| 328 | S | CH₂CH₂NHCH₂ | 2-NO₂-phenyl | 407 |
| 329 | S | CH₂CH₂CH₂NH | 2-NO₂-phenyl | 407 |

TABLE 3-continued

[Structure: 1-(naphthalen-1-yl)-1H-tetrazol-5-yl with X—W—Ar²]

| Entry # | X | W | Ar² | MS ES+ (MH) |
|---------|---|---|-----|-------------|
| 330 | S | CH₂CH(OH)CH₂NH | 2-Cl-phenyl | 412/414 |
| 331 | S | CH₂CH₂NH(CO) | 2-Cl-phenyl | 410/412 |
| 332 | S | CH₂CH₂NMe(CO) | 2-Cl-phenyl | 424/426 |
| 333 | S | CH₂CH₂NH(CO)NH | 2-NO₂-phenyl | 436 |
| 334 | S | CH₂CH₂NH(CO)NH | 2-Cl-phenyl | 425/427 |
| 335 | CH₂ | SCH₂(CO)NH | 2-NO₂-phenyl | 421 |
| 336 | CH₂ | OCH₂(CO)NH | 2-NO₂-phenyl | 405 |
| 337 | CH₂ | NHCH₂(CO)NH | 2-NO₂-phenyl | 404 |
| 338 | CH₂ | N(Me)CH₂(CO)NH | 2-NO₂-phenyl | 418 |
| 339 | S | CH₂ | 1H-benzimidazol-2-yl | 359 |
| 340 | S | CH₂ | 4-NO₂-1H-benzimidazol-2-yl | 404 |
| 341 | S | CH₂CH₂ | phthalimido | 402 |
| 342 | S | CH₂(CO)NMe | 2-Cl-phenyl | 410/412 |
| 343 | — | cyclopropyl-C(O)NH | 2-NO₂-phenyl | 401 |
| 344 | S | CH₂(CO)NHCH₂ | 2-NO₂-phenyl | 421 |

TABLE 3-continued
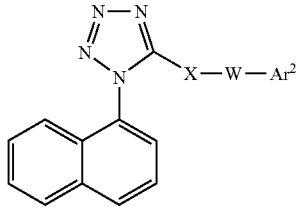
| Entry # | X | W | Ar² | MS ES⁺ (MH) |
|---|---|---|---|---|
| 345 | S | $CH_2(CO)CH_2$ | 2-NO₂-phenyl | 406 |
| 346 | S | 3-pyrrolidinone-1,3-diyl | 2-Cl-phenyl | 422/424 |
TABLE 4
| | | Ar¹—X—W—Ar² | | | |
|---|---|---|---|---|---|
| Entry # | Ar¹ | X | W | Ar² | MS ES⁺ (MH) |
| 401 | 1-(naphthalen-1-yl)imidazol-2-yl | S | $CH_2C(O)NH$ | 2-NO₂-phenyl | 405 |
| 402 | 4-(naphthalen-1-yl)-4H-1,2,4-triazol-3-yl | S | $CH_2C(O)NH$ | 2-NO₂-phenyl | 406 |
| 403 | 5-methyl-4-(naphthalen-1-yl)-4H-1,2,4-triazol-3-yl | S | $CH_2C(O)NH$ | 2-NO₂-phenyl | 420 |
| 404 | 2-(naphthalen-1-yl)furan-3-yl | $CH_2$ | $CH_2C(O)NH$ | 2-NO₂-phenyl | 387 |

TABLE 4-continued
Ar¹—X—W—Ar²
| Entry # | Ar¹ | X | W | Ar² | MS ES⁺ (MH) |
|---|---|---|---|---|---|
| 405 | 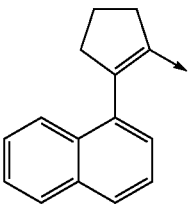 | CH₂ | CH₂C(O)NH | 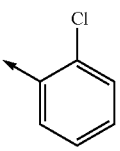 | 376/378 |
| 406 | 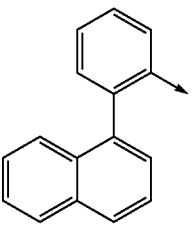 | S | CH₂C(O)NH | 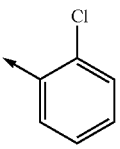 | 404/406 |
| 407 | 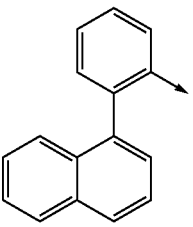 | SO | CH₂C(O)NH | 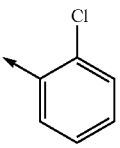 | 420/422 |
| 408 | 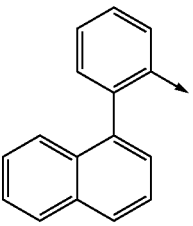 | SO₂ | CH₂C(O)NH | 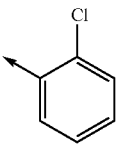 | 436/438 |
| 409 | 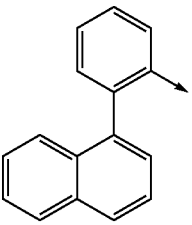 | O | CH₂C(O)NH | 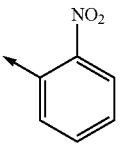 | 399 |
| 410 | 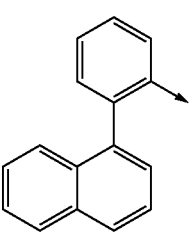 | CH₂ | CH₂C(O)NH | 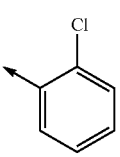 | 386/388 |

TABLE 4-continued

Ar¹—X—W—Ar²

| Entry # | Ar¹ | X | W | Ar² | MS ES⁺ (MH) |
|---|---|---|---|---|---|
| 411 | 1-naphthyl-benzimidazol-2-yl | S | CH₂C(O)NH | 2-NO₂-phenyl | 455 |
| 412 | 1-phenyl-benzimidazol-2-yl | S | CH₂C(O)NH | 2-NO₂-phenyl | 405 |
| 413 | biphenyl-2-yl | O | CH₂C(O)NH | 2-NO₂-phenyl | 349 |
| 414 | 1-naphthyl-imidazol-2-yl | S | CH₂C(O)NH | 2-Me-phenyl | 374 |
| 415 | 1-naphthyl-imidazol-2-yl | S | CH₂C(O)NH | 2-OMe-phenyl | 390 |
| 416 | 2'-chloro-4'-methyl-biphenyl-2-yl | S | CH₂C(O)NH | 2-Cl-phenyl | 402/404/406 |

TABLE 4-continued
Ar¹—X—W—Ar²
| Entry # | Ar¹ | X | W | Ar² | MS ES⁺ (MH) |
|---|---|---|---|---|---|
| 417 | 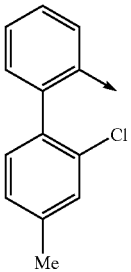 | S | CH₂C(O)NH | 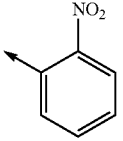 | 413/415 |
| 418 | 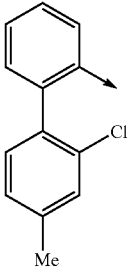 | S | CH₂C(O)NH | 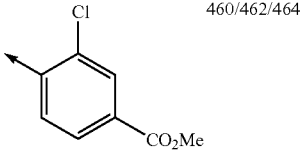 | 460/462/464 |
| 419 | 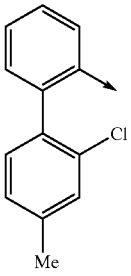 | S | CH₂C(O)NH | 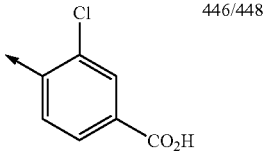 | 446/448 |
| 420 | 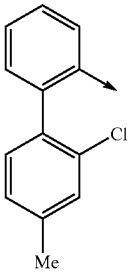 | CH₂ | CH₂C(O)NH | 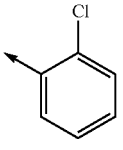 | 385/387 |
| 421 | 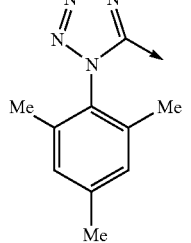 | S | CH₂C(O)NH | 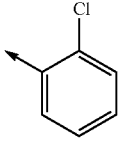 | 388/390 |

TABLE 4-continued

| Entry # | Ar¹ | X | W | Ar² | MS ES⁺ (MH) |
|---|---|---|---|---|---|
| 422 | 1-(2,4,6-trimethylphenyl)tetrazol-5-yl | S | $CH_2C(O)$ | 2-thienyl | 345 |
| 423 | 1-(2,4,6-trimethylphenyl)tetrazol-5-yl | S | $CH_2C(O)$ | benzo[1,3]dioxol-5-yl | 383 |
| 424 | 1-(2,4,6-trimethylphenyl)tetrazol-5-yl | S | $CH_2C(O)$ | benzofuran-2-yl | 379 |
| 425 | 5-ethyl-4-(naphthalen-1-yl)-4H-1,2,4-triazol-3-yl | S | $CH_2C(O)NH$ | 2-nitrophenyl | 434 |
| 426 | 2-bromophenyl | S | $CH_2C(O)NH$ | 2-chlorophenyl | 354/356/358 MS ES⁺ (M − H) |

TABLE 4-continued

| Entry # | Ar¹ | X | W | Ar² | MS ES⁺ (MH) |
|---|---|---|---|---|---|
| 427 | 4-(2-chloro-4-methylphenyl)-3-methyl-4H-1,2,4-triazol-5-yl | S | CH₂C(O)NH | 2-nitrophenyl | 418/420 |
| 428 | 4-(2-chloro-4-methylphenyl)-3-methyl-4H-1,2,4-triazol-5-yl | S | CH₂C(O)NH | 2-chloro-4-phenylphenyl | 483/485/487 |
| 429 | 4-(2-chloro-4-methylphenyl)-3-(2-hydroxyethyl)-4H-1,2,4-triazol-5-yl | S | CH₂C(O)NH | 2-chloro-4-phenylphenyl | 513/515/517 |
| 430 | 4-(2-chloro-4-tert-butylphenyl)-3-methyl-4H-1,2,4-triazol-5-yl | S | CH₂C(O)NH | 2-chlorophenyl | 449/451 |
| 431 | 4-(2-chloro-4-tert-butylphenyl)-3-methyl-4H-1,2,4-triazol-5-yl | S | CH₂C(O)NH | 2-chloro-4-(methylsulfonyl)phenyl | 527/529 |

TABLE 5

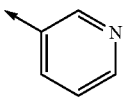

| Entry # | R⁹ | R¹⁰ | MS ES⁺ (MH) |
|---|---|---|---|
| 501 | Cl | H | 394/396/398 |
| 502 | Cl | Me | 408/410/412 |
| 503 | Cl | $CO_2H$ | 438/440/442 |
| 504 | Cl | $CONH_2$ | 437/439/441 |
| 505 | Br | $CO_2H$ | 482/484/486 |
| 506 | $NO_2$ | $CO_2Me$ | 463/465 |
| 507 | $NO_2$ | $CO_2H$ | 449/451 |
| 508 | $NO_2$ | $CONH_2$ | 448/450 |
| 509 | Cl | $SO_2Me$ | 472/474/476 |
| 510 | Cl | Ph | 470/472/474 |
| 511 | Me | Ph | 450/452 |
| 512 | Cl | 3-pyridyl | 471/473/475 |

TABLE 6

| Entry # | R¹⁰ | MS ES⁺ (MH) |
|---|---|---|
| 601 | $(CH_2)_2CO_2H$ | 508/510/512 |
| 602 | $NO_2$ | 481/483/485 |
| 603 | $SO_2Me$ | 514/516/518 |
| 604 | $SO_2NH_2$ | 515/517/— |
| 605 | $SO_2$-(4-chlorophenyl) | 610/612/614 |
| 606 | $SO_2$-phenyl | 576/578/580 |

TABLE 6-continued

| Entry # | R¹⁰ | MS ES⁺ (MH) |
|---|---|---|
| 607 | $SO_2CH(Me)_2$ | 542/544/546 |
| 608 | $SO_2CH_2CH(Me)_2$ | 556/558/560 |
| 609 | $SO_2CH_2CO_2H$ | 573/575/— |
| 610 | 4-methylpiperazin-1-yl | 534/536/538 |
| 611 | morpholin-4-yl | 521/523/525 |
| 612 | pyrrolidin-1-yl | 505/507/509 |
| 613 | piperidin-1-yl | 519/521/523 |
| 614 | 4-Boc-piperazin-1-yl | 620/622/624 |
| 615 | piperazin-1-yl | 520/522/524 |
| 616 | $CO_2H$ | 480/482/484 |
| 617 | $NH_2$ | 451/453/455 |

TABLE 7

General structure: tetrazole-S-CH2-C(=O)-NH-phenyl(R9, R10), N1-R12

| Entry # | R9 | R10 | R12 | MS ES+ (MH) |
|---|---|---|---|---|
| 701 | Cl | H | 2-Br-4-Me-phenyl | 438/440/442 |
| 702 | Cl | H | 2-Br-4-tBu-phenyl | 436/438/440 |
| 703 | Cl | SO2NH2 | 2-Cl-3-Me-5-CF3-phenyl | 541/543/545 |
| 704 | Me | SO2NH2 | 2-Cl-3-Me-5-CF3-phenyl | 521/523 |
| 705 | Cl | H | 2-Cl-4-NEt2-phenyl | 451/453/455 |
| 706 | Cl | H | 2-Cl-4-I-phenyl | 506/508/510 |
| 707 | Cl | H | 2-Cl-4-Et-phenyl | 408/410/412 |
| 708 | Cl | H | 2-Cl-4-allyl-phenyl | 420/422/424 |
| 709 | Cl | H | 2-Cl-4-(3-methylbut-2-enyl)-phenyl | 448/450/452 |

TABLE 8

General structure: tetrazole-S-CH2-C(=O)-NH-Ar2, N1-R12

| Entry # | R12 | Ar2 | MS ES+ (MH) |
|---|---|---|---|
| 801 | 2-Cl-4-tBu-phenyl | 3-chloropyridin-4-yl | 437/439/441 |
| 802 | 2-Cl-4-tBu-phenyl | 2-chloro-6-methylpyridin-3-yl | 451/453/455 |
| 803 | 2-Cl-4-Me-phenyl | 2-chloropyridin-3-yl | 395/397/399 |

Reverse Transcriptase (RT) Assays

Enzymatic Assay ($IC_{50}$)

The enzymatic assay employed is described as follows: The reverse transcriptase (RT) enzyme assay has been adapted to a 96-well microtiter plate format and uses PicoGreen™ as a fluorescent intercalator. More explicitly, the HIV-1 RT enzyme was thawed and appropriately diluted into Tris/HCl 50 mM pH 7.8 containing NaCl 60 mM, $MgCl_2 \circ 6H_2O$ 2 mM, DTT 6 mM, GSH 2 mM and 0.02% w/v Chaps to give ≈10 nM enzyme. To 10 µL of this enzyme solution was added 10 µL of inhibitor solution (40 µM to 78 nM inhibitor in the same assay buffer as above containing 4% v/v DMSO). The plate was pre-incubated for 15 minutes at room temperature before proceeding to the next step. In this pre-incubation step, the highest and lowest inhibitor concentrations were 20 µM and 1.016 nM respectively and the concentration of DMSO was 2% v/v. Then the enzymatic reaction was initiated by addition of 20 µL of substrate solution. The final reaction mixture contained Tris/HCl 50 mM pH 7.8, NaCl 60 mM, $MgCl_2 \circ 6H_2O$ 2 mM, DTT 6 mM, GSH 2 mM, CHAPS 0.02% w/v, DMSO 1% v/v, poly rC 45 nM, $dG_{15}$ 4.5 nM, dGTP 3.6 µM, and ≈2.5 nM enzyme. In this incubation step, the highest and lowest inhibitor concentrations were 10 µM and 0.508 nM respectively. After addition of the substrate cocktail, the plate was covered with a plastic seal and incubated for 50 minutes at 37° C. in a dry incubator. The reaction was then quenched by addition of 5 µL of EDTA 0.5 M. The plate was shaken for 30 seconds at medium speed and incubated for 5 minutes at room temperature. Then 160 µL of PicoGreen™ 1:400 dilution from commercial stock (diluted in Tris 20 mM pH 7.5 with EDTA 1 mM) was added and the plate was shaken for 30 seconds and incubated for 10 minutes at room temperature. The plate was then analyzed using a POLARstar Galaxy fluorimeter (BMG Labtechnologies) with $\lambda_{ex}$ and $\lambda_{em}$ of 485 nm and 520 nm respectively. Each well was read for 1.25 second. Each row contained at its extremities a blank and a control well.

P24 Cellular Assay ($EC_{50}$) (Data Identified with * in Table 9).

The p24 assay is as described in WO 01/96338, the contents of which are herein incorporated by reference.

C8166 HIV-1 Luciferase Assay ($EC_{50}$)

Plasmid: pGL3 Basic LTR/TAR #12

Plasmid is the pGL3 Basic Vector (a promoterless luciferase expression vector from Promega catalogue #E1751) with the addition of HIV-1 HxB2 LTR sequence from nucleotide −138 to +80 (Sca1-HindIII) upstream of the luciferase gene and the gene for blasticidine resistance cloned in.

Cells: C8166 LTRluc #A8-F5-G7

C8166 cells are a human T-lymphotrophic virus type 1 immortalized but nonexpressing line of cord blood lymphocytes and are highly permissive to HIV-1 infection. The reporter cells were made by electroporating C8166 cells with pGL3 Basic LTR/TAR and then selecting positive clones with blasticidine. The clone C8166-LTRluc #A8-F5-G7 was selected by 3 consecutive rounds of limiting dilution under blasticidine selection.

Media: Complete media consisting of: RPMI 1640+10% FBS+$10^{-5}$ M

β-mercaptoethanol+10 µg/ml gentamycin. Cultures are maintained in complete media with 5 µg/ml blasticidine, however, selection is removed for the assay.

Luciferase Assay Protocol

Preparation of Compounds

Serial dilutions of HIV-1 inhibitors compounds are prepared in complete media from 10 mM DMSO stock solutions. Eleven serial dilutions of 2.5x are made at 8x desired final concentration in a 1 ml deep well titer plate (96 wells). The $12^{th}$ well contains complete media with no inhibitor and serves as the positive control. All samples contain the same concentration of DMSO (≦0.1% DMSO). A 25 µl aliquot of inhibitor is added, to triplicate wells, of a 96 well tissue culture treated clear view black microtiter plate (Corning Costar catalogue # 3904). The last row is reserved for uninfected C8166 LTRluc cells to serve as the background blank control and the first row is media alone.

Infection of Cells

Count C8166 LTRluc cells and place in a minimal volume of complete RPMI 1640 in a tissue culture flask (ex. 30×$10^6$ cells in 10 ml media/25 $cm^2$ flask). Infect cells with HIV-1 at a moi of 0.005. Incubate cells for 1.5 hours at 37° C. on a rotating rack in a 5% $CO_2$ incubator. Resuspend cells in complete RPMI to give a final concentration of 25,000-cells/ 175 µl. Add 175 µl of cell mix to wells of 96 well microtiter plate containing 25 µl 8x inhibitors. Add 25,000 uninfected C8166-LTRluc cells/well in 200 µl complete RPMI to last row for background control. Incubate cells at 37° C. in 5% $CO_2$ incubator for 3 days.

Luciferase Assay

Add 50 µl Steady Glo (luciferase substrate $T_{1/2}$=5 hours Promega catalogue # E2520) to each well of the 96 well plate. Determine the relative light units (RLU) of luciferase using the BMG LUMlstar Galaxy luminometer. Plates are read from the bottom for 2 seconds per well with a gain of 240.

The level of inhibition (% inhibition) of each well containing inhibitor was calculated with the following equation:

$$\% \cdot \text{inhibition} = \left(1 - \left[\frac{RLU \cdot \text{well} - RLU \cdot \text{blank}}{RLU \cdot \text{control} - RLU \cdot \text{blank}}\right]\right) * 100$$

The calculated % inhibition values were then used to determine $EC_{50}$, slope factor (n) and maximum inhibition ($I_{max}$) by the non-linear regression routine NLIN procedure of SAS using the following equation:

$$\% \cdot \text{inhibition} = \frac{I_{max} \times [\text{inhibitor}]^n}{[\text{inhibitor}]^n + IC_{50}^n}$$

The results are listed in Table 9 as $IC_{50}$(nM) and $EC_{50}$ (nM).

Table legend: A=>100; B=100-50; C=<50; NT=not tested

According to this invention those compounds are preferred which possess an $IC_{50}$ value against the resistant mutant K103N/Y181C smaller than 50 nM (range C), most preferably an $EC_{50}$ value against the resistant mutant K103N/Y181C smaller than 50 nM (range C).

TABLE 9

| Entry # | $IC_{50}$ WT | $IC_{50}$ K103N/Y181C | $EC_{50}$ WT | $EC_{50}$ K103N/Y181C |
|---|---|---|---|---|
| 101 | C | A | C* | A* |
| 102 | C | A | C* | NT |
| 103 | C | A | C* | A* |
| 104 | C | A | C* | A* |
| 105 | C | A | C* | A* |
| 106 | A | NT | NT | NT |
| 107 | A | NT | NT | NT |
| 108 | A | A | NT | NT |
| 109 | B | A | C* | A* |
| 110 | A | A | NT | NT |
| 111 | B | A | C* | A* |
| 112 | A | A | NT | NT |
| 113 | C | A | C* | NT |
| 114 | C | A | C* | A* |

TABLE 9-continued

| Entry # | IC$_{50}$ WT | IC$_{50}$ K103N/Y181C | EC$_{50}$ WT | EC$_{50}$ K103N/Y181C |
|---|---|---|---|---|
| 115 | B | A | C* | A* |
| 116 | C | A | C* | NT |
| 117 | C | A | NT | A* |
| 118 | B | A | C* | A* |
| 119 | A | A | NT | NT |
| 120 | A | NT | NT | NT |
| 121 | A | NT | NT | NT |
| 122 | C | A | C* | A* |
| 123 | C | A | NT | B* |
| 124 | C | A | C* | B* |
| 125 | C | A | C* | A* |
| 126 | A | A | NT | NT |
| 127 | C | A | C* | A* |
| 128 | A | A | C* | A* |
| 129 | C | A | C* | C* |
| 130 | C | A | C* | NT |
| 131 | A | NT | NT | NT |
| 132 | A | NT | NT | NT |
| 133 | C | A | C* | A* |
| 134 | C | A | C* | A* |
| 135 | C | A | C* | A* |
| 136 | B | A | C* | A* |
| 137 | A | A | NT | NT |
| 138 | A | NT | NT | NT |
| 139 | C | A | C* | NT |
| 140 | C | A | C* | C* |
| 141 | A | A | C* | C* |
| 142 | NT | A | C | A |
| 143 | NT | A | C | A |
| 144 | C | A | NT | NT |
| 145 | C | A | C | A |
| 146 | C | B | C | B |
| 147 | C | A | C | B |
| 201 | A | A | NT | NT |
| 202 | A | A | NT | NT |
| 203 | A | NT | NT | NT |
| 204 | A | NT | NT | NT |
| 205 | A | NT | NT | NT |
| 206 | A | NT | NT | NT |
| 207 | A | NT | NT | NT |
| 208 | C | NT | C | A |
| 209 | C | NT | A* | NT |
| 210 | B | NT | C* | A* |
| 211 | A | NT | C | A |
| 212 | A | NT | NT | NT |
| 213 | A | NT | NT | NT |
| 214 | A | NT | NT | NT |
| 215 | A | NT | NT | NT |
| 216 | A | NT | NT | NT |
| 217 | A | NT | NT | NT |
| 218 | A | NT | NT | NT |
| 219 | A | NT | NT | NT |
| 220 | A | NT | NT | NT |
| 221 | A | NT | NT | NT |
| 222 | A | NT | NT | NT |
| 223 | A | NT | NT | NT |
| 224 | A | NT | NT | NT |
| 225 | A | NT | NT | NT |
| 226 | A | NT | NT | NT |
| 227 | A | NT | NT | NT |
| 228 | A | NT | NT | NT |
| 229 | A | NT | NT | NT |
| 230 | B | NT | B* | A* |
| 231 | B | NT | C* | A* |
| 232 | A | NT | NT | NT |
| 233 | A | NT | NT | NT |
| 234 | B | NT | B* | A* |
| 235 | C | A | C* | NT |
| 236 | B | A | A* | A* |
| 237 | C | A | C | NT |
| 238 | C | A | B | A |
| 239 | B | A | C* | A* |
| 240 | A | A | NT | NT |
| 241 | A | NT | NT | NT |
| 242 | A | NT | NT | NT |
| 243 | A | NT | NT | NT |
| 244 | A | NT | NT | NT |
| 245 | A | NT | NT | NT |
| 246 | C | A | C | A |
| 301 | B | A | C* | A* |
| 302 | A | A | B* | NT |
| 303 | A | NT | NT | NT |
| 304 | A | NT | NT | NT |
| 305 | A | NT | NT | NT |
| 306 | A | NT | NT | NT |
| 307 | A | NT | NT | NT |
| 308 | A | NT | B* | NT |
| 309 | A | NT | NT | NT |
| 310 | A | NT | NT | NT |
| 311 | A | NT | NT | NT |
| 312 | A | NT | NT | NT |
| 313 | A | NT | NT | NT |
| 314 | A | NT | NT | NT |
| 315 | A | NT | NT | NT |
| 316 | B | A | C* | NT |
| 317 | B | A | C* | NT |
| 318 | B | A | C* | NT |
| 319 | A | NT | NT | NT |
| 320 | A | NT | NT | NT |
| 321 | A | NT | NT | NT |
| 322 | A | NT | NT | NT |
| 323 | A | NT | NT | NT |
| 324 | A | NT | NT | NT |
| 325 | A | A | NT | NT |
| 326 | A | NT | NT | NT |
| 327 | A | NT | NT | NT |
| 328 | A | NT | NT | NT |
| 329 | A | NT | NT | NT |
| 330 | B | A | C* | NT |
| 331 | A | NT | NT | NT |
| 332 | A | NT | NT | NT |
| 333 | A | NT | NT | NT |
| 334 | A | NT | NT | NT |
| 335 | A | NT | NT | NT |
| 336 | A | NT | NT | NT |
| 337 | A | NT | NT | NT |
| 338 | A | NT | NT | NT |
| 339 | A | NT | NT | NT |
| 340 | A | NT | NT | NT |
| 341 | A | NT | NT | NT |
| 342 | A | NT | NT | NT |
| 343 | A | NT | NT | NT |
| 344 | A | NT | NT | NT |
| 345 | A | NT | NT | NT |
| 346 | A | NT | NT | NT |
| 401 | A | A | C* | NT |
| 402 | B | A | C* | A* |
| 403 | C | A | C | A |
| 404 | A | NT | NT | NT |
| 405 | A | NT | NT | NT |
| 406 | C | A | A | NT |
| 407 | A | NT | NT | NT |
| 408 | A | NT | NT | NT |
| 409 | A | NT | A* | NT |
| 410 | A | NT | NT | NT |
| 411 | A | A | NT | NT |
| 412 | A | NT | NT | NT |
| 413 | A | A | NT | NT |
| 414 | A | NT | NT | NT |
| 415 | A | NT | NT | NT |
| 416 | C | A | C | A |
| 417 | C | A | C | A |
| 418 | C | A | B | NT |
| 419 | C | A | B | NT |
| 420 | A | NT | NT | NT |
| 421 | C | A | C* | A* |
| 422 | A | NT | NT | NT |
| 423 | A | NT | NT | NT |
| 424 | A | NT | NT | NT |
| 425 | NT | A | C | A |
| 426 | A | NT | NT | NT |
| 427 | NT | A | C | A |

TABLE 9-continued

| Entry # | IC$_{50}$ WT | IC$_{50}$ K103N/Y181C | EC$_{50}$ WT | EC$_{50}$ K103N/Y181C |
|---|---|---|---|---|
| 428 | NT | A | C | A |
| 429 | C | A | C | A |
| 430 | C | B | C | B |
| 431 | C | B | C | C |
| 501 | C | A | C | A |
| 502 | C | A | C | NT |
| 503 | C | A | C | A |
| 504 | C | A | C | C |
| 505 | C | A | C | A |
| 506 | C | A | NT | NT |
| 507 | C | A | C | A |
| 508 | C | B | C | C |
| 509 | C | A | C | A |
| 510 | C | B | C | A |
| 511 | C | A | C | A |
| 512 | C | A | C | A |
| 601 | C | A | C | A |
| 602 | C | A | B | A |
| 603 | C | C | C | C |
| 604 | C | C | C | C |
| 605 | C | A | B | A |
| 606 | C | B | C | B |
| 607 | C | A | C | B |
| 608 | C | A | C | B |
| 609 | NT | B | NT | NT |
| 610 | C | A | C | A |
| 611 | C | A | C | A |
| 612 | C | A | B | A |
| 613 | C | A | C | A |
| 614 | C | A | C | A |
| 615 | C | A | C | A |
| 616 | C | B | C | C |
| 617 | C | A | C | B |
| 701 | C | A | NT | NT |
| 702 | C | B | C | A |
| 703 | C | B | C | C |
| 704 | B | A | NT | NT |
| 705 | C | A | C | A |
| 706 | C | A | C | A |
| 707 | C | A | C | A |
| 708 | C | A | C | A |
| 709 | C | A | A | A |
| 801 | C | C | C | C |
| 802 | C | A | C | B |
| 803 | NT | A | C | A |

What is claimed is:

1. A compound of formula 1:

Ar$^1$—X—W—Ar$^2$  1 wherein Ar$^1$ is

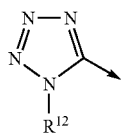

wherein R$^{12}$ is selected from the group consisting of

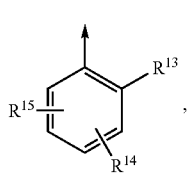 , 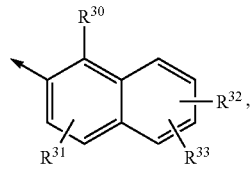

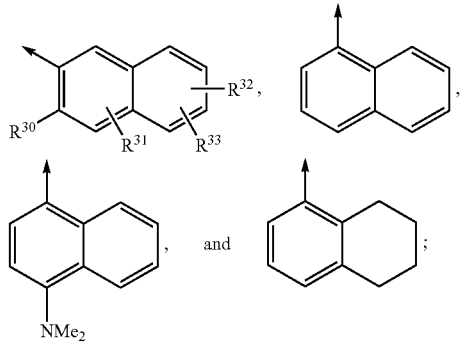

R$^{13}$ represents Cl, Br, COO(C$_{1-4}$)alkyl and
  if R$^9$ is NO$_2$, Cl or Br, then R$^{13}$ may also represent F or CH$_3$;
R$^{14}$, R$^{15}$,
R$^{31}$, R$^{32}$,
R$^{33}$ are each independently selected from the group consisting of H, (C$_{1-6}$)alkyl, (C$_{3-7}$)cycloalkyl, (C$_{3-7}$)cycloalkyl-(C$_{1-3}$)alkyl, (C$_{2-6}$)alkenyl, O—(C$_{1-4}$)alkyl, S-(C$_{1-4}$)alkyl, halo, CF$_3$, OCF$_3$, OH, NO$_2$, CN, SO$_2$NH$_2$, SO$_2$—(C$_{1-4}$)alkyl, C(O)OR$^1$ wherein R$^1$ is H or (C$_{1-4}$)alkyl, or NR$^2$R$^3$ wherein R$^2$ and R$^3$ each independently is H or (C$_{1-4}$)alkyl;
R$^{30}$ represents H, Cl, Br, COO(C$_{1-4}$)alkyl; and
X is S or O;
W is CH$_2$C(O)NR$^6$ wherein R$^6$ is H or (C$_{1-4}$)alkyl; and
Ar$^2$ is selected from the group consisting of

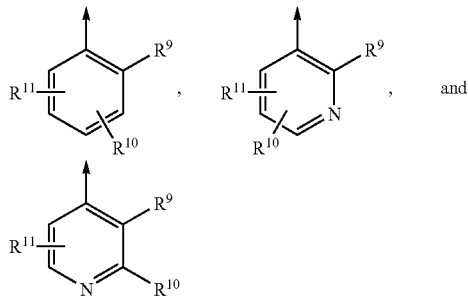

wherein R$^9$ is halo or NO$_2$; and if R$^{13}$ is Cl or Br, then R$^9$ may also represent (C$_{1-3}$)alkyl;
R$^{10}$, R$^{11}$ are independently of each other selected from the group consisting of H, (C$_{1-6}$)alkyl, (C$_{3-7}$)Cycloalkyl, (C$_{3-7}$)Cycloalkyl-(C$_{1-3}$)alkyl, (C$_{2-6}$)alkenyl, O(C$_{1-6}$)alkyl, S(C$_{1-6}$)alkyl, halo, CF$_3$, OCF$_3$, OH, NO$_2$, CN, —NR$^{N1}$R$^{N2}$, —C(O)R$^{21}$, —(C$_{1-3}$)alkyl-C(O)R$^{21}$, —C(O)OR$^{22}$, —(C$_{1-3}$)alkyl-C(O)OR$^{22}$, —SO$_2$—(C$_{1-3}$)alkyl-C(O)OR$^{22}$, wherein R$^{21}$ is (C$_{1-4}$)alkyl and R$^{22}$ is H or (C$_{1-4}$)alkyl;
—(C$_{1-3}$)alkyl-C(O)NH$_2$, C(O)NH$_2$, S(O)—(C$_{1-6}$)alkyl, —SO$_2$—(C$_{1-6}$)alkyl, —SO$_2$-phenyl, —SO$_2$—NH$_2$, phenyl, phenylmethyl, 2-, 3- or 4-pyridinyl, 1-pyrrolyl, whereby said phenyl, pyridinyl and pyrrolyl may have one or more substituents selected from the group consisting of halo, NO$_2$, C$_{1-3}$-alkyl and CF$_3$;
wherein R$^{N1}$, R$^{N2}$ each independently represent H or (C$_{1-6}$)alkyl, whereby R$^{N1}$ and R$^{N2}$ may be covalently bonded to each other to form together with the N-atom to which they are attached to a 4 to 7-membered heterocycle whereby the —CH$_2$-group at the position 4 of a 6 or 7-membered heterocycle may be replaced by —O—, —S— or —NR$^{N3}$- wherein R$^{N3}$ represents H, —C(O)OR$^{22}$, (C$_{1-6}$)alkyl,(C$_{3-7}$)cycloalkyl or (C$_{3-7}$)cycloalkyl-(C$_{1-3}$)alkyl, wherein R$^{22}$ is H or (C$_{1-4}$)alkyl;

or a pharmaceutically acceptable salt thereof.

2. The compound of formula 1 according to claim 1 wherein Ar$^1$ is

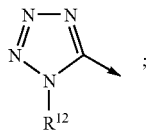

and wherein R$^{12}$ is selected from the group consisting of

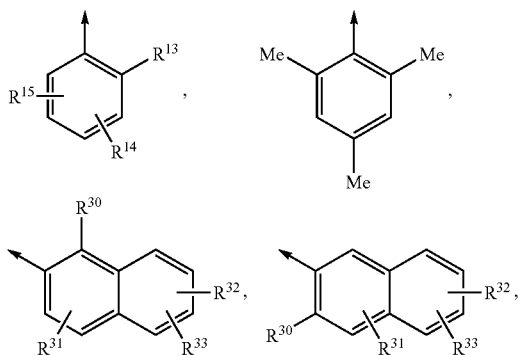

wherein R$^{13}$, R$^{14}$, R$^{15}$, R$^{30}$, R$^{31}$, R$^{32}$ and R$^{33}$ are as defined in claim 1.

3. The compound of formula 1 according to claim 2 wherein

R$^{13}$ represents Cl or Br and if R$^9$ is NO$_2$, Cl or Br, then R$^{13}$ may also represent F or CH$_3$;

R$^{14}$, R$^{15}$,

R$^{31}$, R$^{32}$,

R$^{33}$ are each independently selected from the group consisting of H, (C$_{1-6}$)alkyl, (C$_{3-7}$)cycloalkyl, (C$_{3-7}$)cycloalkyl-(C$_{1-3}$)alkyl, (C$_{2-6}$)alkenyl, O —(C$_{1-4}$)alkyl, S—(C$_{1-4}$)alkyl, halo, CF$_3$, OCF$_3$, OH, NO$_2$, CN, SO$_2$NH$_2$, SO$_2$—(C$_{1-4}$)alkyl, C(O)OR$^1$ wherein R$^1$ is H or (C$_{1-4}$)alkyl, or NR$^2$R$^3$ wherein R$^2$ and R$^3$ each independently is H or (C$_{1-4}$)alkyl; and R$^{30}$ represents Cl or Br.

4. The compound of formula 1 according to claim 3 wherein W is CH$_2$C(O)NH.

5. A compound according to claim 1 wherein

Ar$^1$ is defined as

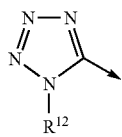

and wherein R$^{12}$ is selected from the group consisting of

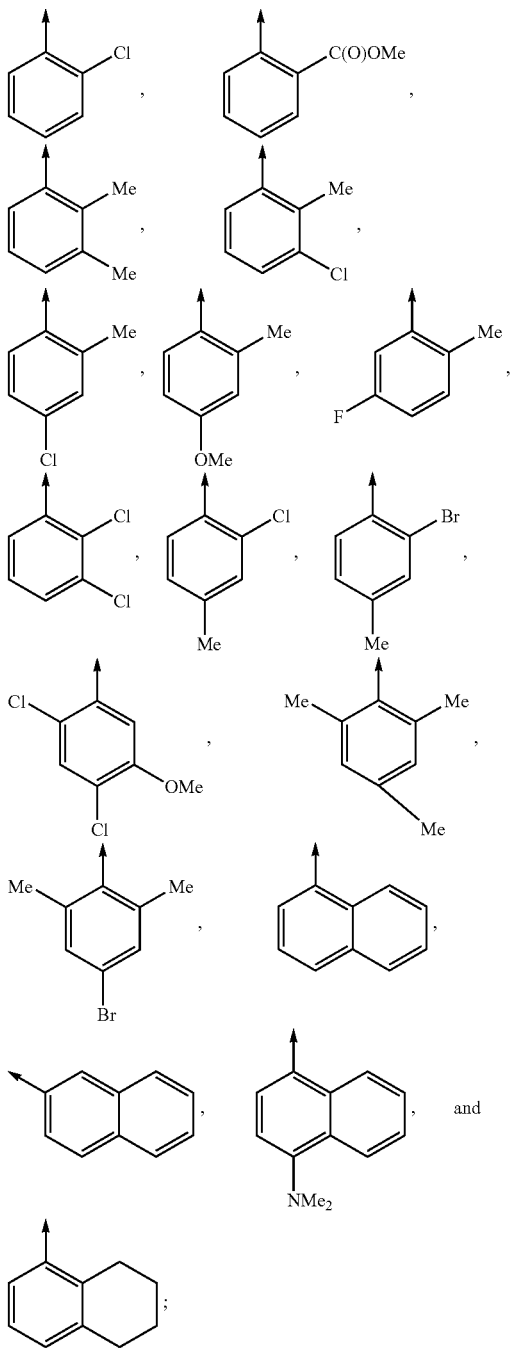

X is S;

W is CH$_2$C(O)NR$^6$ wherein R$^6$ is H or (C$_{1-4}$)alkyl; and

Ar$^2$ is

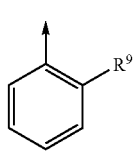

wherein R⁹ is halo or NO₂; or
Ar² is

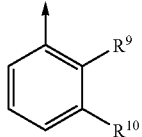

wherein R⁹ is halo or NO₂ and R¹⁰ is halo; or
Ar² is

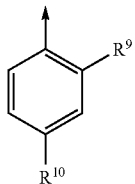

wherein R⁹ is halo or NO₂, and R¹⁰ is OMe, halo, OH, NO₂, phenyl, C(O)OH or C(O)OMe.

6. A compound of formula 1, according to claim 1, wherein Ar¹ is:

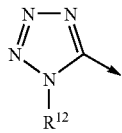

and wherein R¹² selected from the group consisting of:

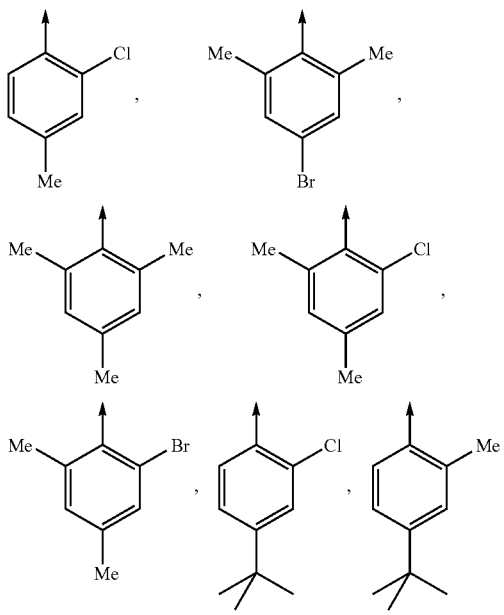

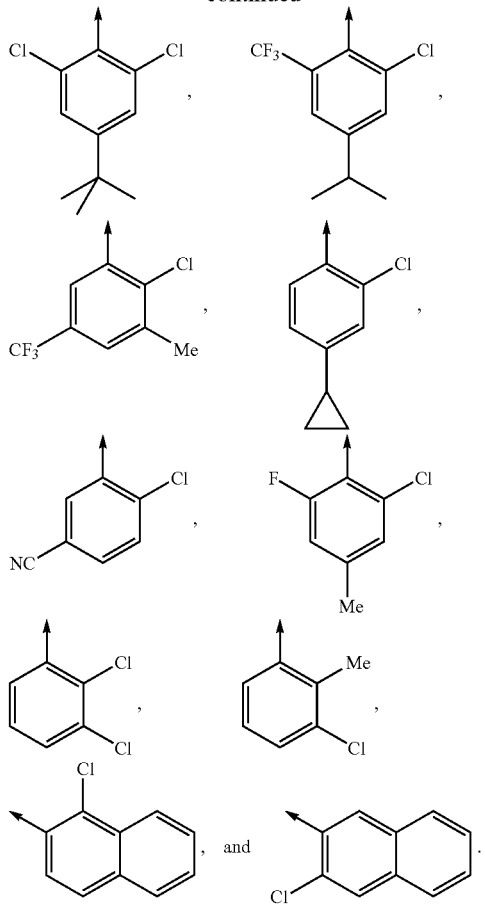

7. A compound of formula 1, according to claim 1, wherein Ar² is selected from the group consisting of

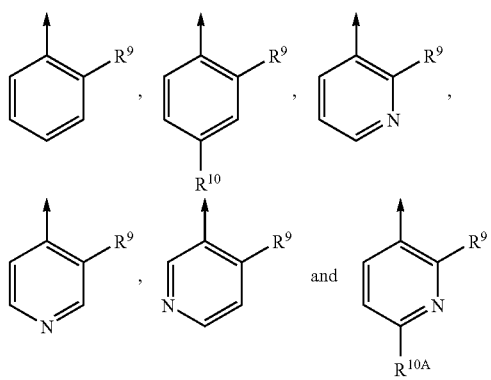

wherein R⁹ is Cl or NO₂ and
R$^{10A}$ is C$_{1-4}$alkyl;
R¹⁰ is selected from the group consisting of (C$_{1-4}$)alkyl, (C$_{3-4}$)cycloalkyl, (C$_{3-7}$)cycloalkyl-(C$_{1-3}$)alkyl, (C$_{2-6}$) alkenyl, O(C$_{1-6}$)alkyl, S(C$_{1-6}$)alkyl, halo, CF₃, OCF₃, OH, NO₂, CN, —NR$^{N1}$R$^{N2}$, —C(O)R²¹, —(C$_{1-3}$)alkyl-C(O)R²¹, —C(O)OR²², —(C$_{1-3}$)alkyl- C(O)OR²², —SO₂—(C$_{1-3}$)alkyl-C(O)OR²², —(C$_{1-3}$)alkyl-C(O) NH₂, C(O)NH₂, —S(O)—(C$_{1-6}$)alkyl, —SO₂—(C$_{1-6}$) alkyl, —SO₂-phenyl, —SO₂—NH₂, phenyl, phenylmethyl, 2-, 3- or 4-pyridinyl, 1-pyrrolyl, whereby said phenyl, pyridinyl and pyrrolyl may have one or more substituents selected from the group consisting of halo, $NO_2$, $C_{1-3}$-alkyl and $CF_3$;

wherein $R^{21}$ is $(C_{1-4})$alkyl and $R^{22}$ is H or $(C_{1-4})$alkyl;

wherein $R^{N1}$, $R^{N2}$ each independently represent H or $(C_{1-6})$alkyl, whereby $R^{N1}$ and $R^{N2}$ may be covalently bonded to each other to form together with the N-atom to which they are attached to a 4 to 7-membered heterocycle whereby the —$CH_2$-group at the position 4 of a 6 or 7-membered heterocycle may be replaced by —O—, —S— or —$NR^{N3}$— wherein $R^{N3}$ represents H, —C(O)$OR^{22}$, $(C_{1-6})$alkyl, $(C_{3-7})$cycloalkyl or $(C_{3-7})$cycloalkyl-$(C_{1-3})$alkyl, wherein $R^{22}$ is H or $(C_{1-4})$alkyl.

8. A compound of formula 1, according to claim 7, wherein $Ar^2$ is:

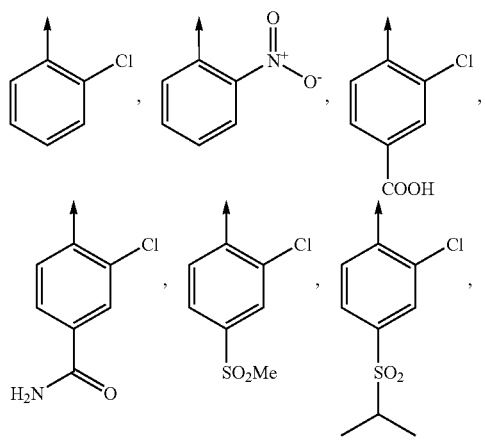

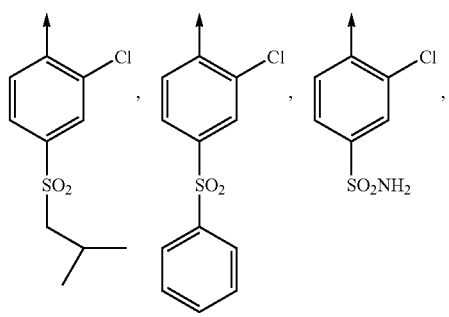

-continued

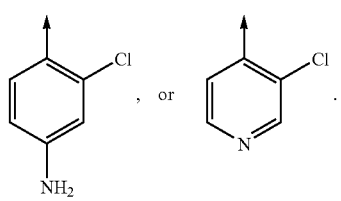

9. A pharmaceutical composition comprising a compound of formula 1 as defined in claim 1, or a pharmaceutically acceptable salt thereof, and optionally one or more pharmaceutically acceptable carriers.

10. A pharmaceutical composition for the treatment of HIV infection, comprising a compound of formula 1 as defined in claim 1, or a pharmaceutically acceptable salt thereof.

* * * * *